US012672820B2

(12) United States Patent
Miller

(10) Patent No.: US 12,672,820 B2
(45) Date of Patent: *Jul. 7, 2026

(54) SYSTEMS AND METHODS FOR DETECTING DRUG BASED IMPAIRMENT

(71) Applicant: BI Incorporated, Boulder, CO (US)

(72) Inventor: Ric Miller, Boulder, CO (US)

(73) Assignee: BI Incorporated, Boulder, CO (US)

( * ) Notice: Subject to any disclaimer, the term of this patent is extended or adjusted under 35 U.S.C. 154(b) by 473 days.

This patent is subject to a terminal disclaimer.

(21) Appl. No.: 18/201,032

(22) Filed: May 23, 2023

(65) Prior Publication Data

US 2023/0389818 A1 Dec. 7, 2023

Related U.S. Application Data

(60) Provisional application No. 63/393,505, filed on Jul. 29, 2022, provisional application No. 63/393,519, (Continued)

(51) Int. Cl.
A61B 5/08 (2006.01)
A61B 5/00 (2006.01)
(Continued)

(52) U.S. Cl.
CPC .......... *A61B 5/4845* (2013.01); *A61B 5/0077* (2013.01); *A61B 5/082* (2013.01); *A61B 5/097* (2013.01); *A61B 5/11* (2013.01); *A61B 5/4803* (2013.01); *A61B 5/4833* (2013.01); *A61B 5/7267* (2013.01); *A61B 5/7275* (2013.01); *G06V 10/764* (2022.01); *G06V 10/774*

(2022.01); *G06V 20/44* (2022.01); *G06V 20/52* (2022.01); *G06V 40/172* (2022.01); *G10L 15/063* (2013.01); *G10L 15/22* (2013.01); *G10L 25/51* (2013.01); *G16H 40/67* (2018.01); *A61B 2010/0087* (2013.01); *A61B 2562/0204* (2013.01)

(58) Field of Classification Search
USPC .................................................. 73/23.3, 23.6
See application file for complete search history.

(56) References Cited

U.S. PATENT DOCUMENTS 4,724,427 A 2/1988 Carroll
5,731,757 A * 3/1998 Layson, Jr. ............ G08B 21/22
340/8.1

(Continued)

FOREIGN PATENT DOCUMENTS

JP 2018/505759 A 3/2018
WO WO/1998/08204 2/1998
(Continued)

*Primary Examiner* — Walter L Lindsay, Jr.
*Assistant Examiner* — Warren K Fenwick
(74) *Attorney, Agent, or Firm* — Osha Bergman Watanabe & Burton LLP

(57) ABSTRACT

Various embodiments provide systems and methods for identifying impairment using measurement devices and trained models, and/or for indicating interference with impairment testing. Embodiments discussed herein provide systems, methods, and/or devices that enable remote impairment testing that does not require a human monitor to be present or physically near the individual being monitored. Such an ability is an improvement.

20 Claims, 18 Drawing Sheets

Related U.S. Application Data filed on Jul. 29, 2022, provisional application No. 63/393,498, filed on Jul. 29, 2022, provisional application No. 63/393,513, filed on Jul. 29, 2022, provisional application No. 63/389,258, filed on Jul. 14, 2022, provisional application No. 63/349,496, filed on Jun. 6, 2022.

(51) Int. Cl.

| | |
|---|---|
| *A61B 5/097* | (2006.01) |
| *A61B 5/11* | (2006.01) |
| *G06V 10/764* | (2022.01) |
| *G06V 10/774* | (2022.01) |
| *G06V 20/40* | (2022.01) |
| *G06V 20/52* | (2022.01) |
| *G06V 40/16* | (2022.01) |
| *G10L 15/06* | (2013.01) |
| *G10L 15/22* | (2006.01) |
| *G10L 25/51* | (2013.01) |
| *G16H 40/67* | (2018.01) |
| *A61B 10/00* | (2006.01) |

(56) References Cited

U.S. PATENT DOCUMENTS

| | | | |
|---|---|---|---|
| 6,130,620 | A | 10/2000 | Pinnow |
| 6,169,484 | B1 | 1/2001 | Schuman |
| 6,323,773 | B1 | 11/2001 | Runyon |
| 6,393,362 | B1 | 5/2002 | Burns |
| 6,405,213 | B1 * | 6/2002 | Layson ............... G08B 21/0211 |
| | | | 340/8.1 |
| 7,015,817 | B2 | 3/2006 | Copely |
| 7,619,533 | B2 | 11/2009 | Crucilla |
| 7,886,648 | B2 | 2/2011 | Williams |
| 7,905,832 | B1 | 3/2011 | Lau |
| 7,930,927 | B2 | 4/2011 | Cooper |
| 8,352,111 | B2 | 1/2013 | Mudalige |
| 8,493,219 | B2 | 7/2013 | Buck |
| 8,576,065 | B2 | 11/2013 | Buck |
| 8,629,776 | B2 | 1/2014 | Buck |
| 8,657,744 | B2 | 2/2014 | Rompa et al. |
| 8,899,748 | B1 | 12/2014 | Migdal |
| 8,952,805 | B2 | 2/2015 | Baines et al. |
| 9,135,803 | B1 | 9/2015 | Fields |
| 9,240,118 | B2 | 1/2016 | Melton |
| 9,241,659 | B2 | 1/2016 | Rompa et al. |
| 9,355,548 | B2 | 5/2016 | Buck |
| 9,423,487 | B2 | 8/2016 | Buck |
| 9,626,855 | B2 | 4/2017 | Melton |
| 9,629,420 | B2 | 4/2017 | Cooper |
| 9,668,095 | B1 | 5/2017 | Newell |
| 9,884,626 | B2 | 2/2018 | Grant |
| 9,974,478 | B1 | 5/2018 | Brokaw |
| 9,989,649 | B2 | 6/2018 | Buck |
| 10,037,676 | B1 | 7/2018 | Scharf |
| 10,068,462 | B2 | 9/2018 | Buck |
| 10,368,744 | B1 | 8/2019 | Miller |
| 2003/0222781 | A1 | 12/2003 | Defant et al. |
| 2005/0040944 | A1 | 2/2005 | Contestabile |
| 2007/0014264 | A1 | 1/2007 | Davis |
| 2007/0132950 | A1 | 6/2007 | Victor |
| 2007/0285258 | A1 | 12/2007 | Hartman |
| 2008/0012760 | A1 | 1/2008 | Derrick |
| 2008/0018459 | A1 | 1/2008 | Victor |
| 2011/0154887 | A1 | 6/2011 | Cooper |
| 2011/0195722 | A1 | 8/2011 | Walter et al. |
| 2011/0199205 | A1 | 8/2011 | Kremi |
| 2011/0237726 | A1 | 9/2011 | Dhuna |
| 2011/0304465 | A1 | 12/2011 | Bopult |
| 2013/0006066 | A1 | 1/2013 | Melton |
| 2013/0031422 | A1 | 1/2013 | Church |
| 2013/0035613 | A1 | 2/2013 | Crrtiss |
| 2013/0328678 | A1 | 12/2013 | Shechtner |
| 2014/0039804 | A1 | 2/2014 | Park |
| 2014/0121559 | A1 | 5/2014 | Stevensen |
| 2014/0179342 | A1 | 6/2014 | Hamerly |
| 2014/0249447 | A1 | 9/2014 | Serenso |
| 2015/0005674 | A1 | 1/2015 | Schlindlar |
| 2015/0048978 | A1 | 2/2015 | Buck et al. |
| 2015/0061864 | A1 | 3/2015 | Buck et al. |
| 2015/0078622 | A1 | 3/2015 | Buck et al. |
| 2015/0123766 | A1 | 5/2015 | St John |
| 2015/0131085 | A1 | 5/2015 | Cooper et al. |
| 2015/0212063 | A1 * | 7/2015 | Wojcik ................. G06V 40/167 |
| | | | 340/576 |
| 2015/0228184 | A1 | 8/2015 | Buck et al. |
| 2015/0279200 | A1 | 10/2015 | Buck et al. |
| 2015/0327214 | A1 | 11/2015 | Buck et al. |
| 2015/0356261 | A1 | 12/2015 | Brust |
| 2016/0154643 | A1 | 6/2016 | Zhang |
| 2016/0166204 | A1 | 6/2016 | Stevens |
| 2016/0267770 | A1 | 9/2016 | Keays |
| 2016/0301581 | A1 | 10/2016 | Carter |
| 2016/0318521 | A1 | 11/2016 | Nothacker |
| 2016/0339922 | A1 | 11/2016 | Schmidt |
| 2017/0020442 | A1 | 1/2017 | Flitsch |
| 2017/0049362 | A1 | 2/2017 | Macknik |
| 2017/0134249 | A1 | 5/2017 | Lang |
| 2017/0135620 | A1 * | 5/2017 | Bae ...................... A61B 5/7264 |
| 2017/0188845 | A1 | 7/2017 | Banet |
| 2017/0229041 | A1 | 8/2017 | Reichow |
| 2017/0265798 | A1 | 9/2017 | Sales |
| 2017/0303090 | A1 | 10/2017 | Stitt |
| 2017/0307388 | A1 | 10/2017 | McConathy |
| 2018/0028106 | A1 | 2/2018 | Leschinsky |
| 2018/0224517 | A1 | 8/2018 | Ingerson |
| 2018/0296134 | A1 | 10/2018 | Schuster |
| 2019/0043285 | A1 | 2/2019 | Hodge |
| 2019/0159672 | A1 | 5/2019 | Macknik |
| 2019/0184231 | A1 | 6/2019 | Borroughs |
| 2019/0192062 | A1 | 6/2019 | Felsing |
| 2019/0205617 | A1 | 7/2019 | Bertan |
| 2019/0279480 | A1 | 9/2019 | Lee |
| 2020/0121235 | A1 | 4/2020 | Gibbons |
| 2020/0129107 | A1 | 4/2020 | Bunn |
| 2020/0237291 | A1 | 7/2020 | Sundaram |
| 2020/0289042 | A1 | 9/2020 | Patton |
| 2021/0182625 | A1 * | 6/2021 | Arar ...................... G06V 20/647 |
| 2022/0218253 | A1 * | 7/2022 | Seidenspinner ....... G06V 20/41 |
| 2023/0389865 | A1 * | 12/2023 | Miller .................. A61B 5/4803 |
| 2023/0389866 | A1 * | 12/2023 | Miller .................. G06V 10/764 |
| 2023/0389867 | A1 * | 12/2023 | Miller .................... G16H 50/20 |
| 2023/0394825 | A1 * | 12/2023 | Miller .................... A61B 5/117 |
| 2023/0394876 | A1 * | 12/2023 | Miller .................. A61B 5/0077 |

FOREIGN PATENT DOCUMENTS

| | | |
|---|---|---|
| WO | WO/2000/077688 | 12/2000 |
| WO | WO/2007/135462 | 11/2007 |

* cited by examiner

1352

1354

1356

1358

SYSTEMS AND METHODS FOR DETECTING DRUG BASED IMPAIRMENT

CROSS REFERENCE TO RELATED APPLICATION

The present application claims priority to (i.e., is a non-provisional of) U.S. Pat. App. No. 63/389,258 entitled "Systems and Methods for Detecting Alcohol Sensor Interference", and filed Jul. 14, 2022 by Miller; U.S. Pat. App. No. 63/349,496 entitled "Systems and Methods For Detect Drug Use Via Breath Sample with Remote Biometric", and filed Jun. 6, 2022 by Miller et al; U.S. Pat. App. No. 63/393,498 entitled "Systems and Methods for Learning and Classifying VOCs in Breath", and filed Jul. 29, 2022 by Miller; U.S. Pat. App. No. 63/393,505 entitled "Systems and Methods for Classifying Voice Slurring", and filed Jul. 29, 2022 by Miller; U.S. Pat. App. No. 63/393,513 entitled "Systems and Methods for Learning and Classifying User Movement", and filed Jul. 29, 2022 by Miller; and U.S. Pat. App. No. 63/393,519 entitled "Systems and Methods Learning and Classifying Facial Expressions", and filed Jul. 29, 2022 by Miller. The entirety of each of the aforementioned references are incorporated herein by reference for all purposes.

BACKGROUND OF THE INVENTION

Various embodiments provide systems and methods for identifying impairment using measurement devices and trained models, and/or for indicating interference with impairment testing.

Large numbers of individuals are currently monitored as part of parole requirements or other requirements. Such monitoring allows a monitoring agency to determine whether the individual is engaging in acceptable patterns of behavior, and where an unacceptable behavior is identified to stop such behavior going forward. It is common to obtain samples from an individual to prove or disprove use of drugs or alcohol. It is also common for an individual to attempt to defeat such testing.

Thus, for at least the aforementioned reasons, there exists a need in the art for more advanced approaches, devices and systems for monitoring potential impairment of individuals.

BRIEF SUMMARY OF THE INVENTION

Various embodiments provide systems and methods for identifying impairment using measurement devices and trained models, and/or for indicating interference with impairment testing.

This summary provides only a general outline of some embodiments. Many other objects, features, advantages and other embodiments will become more fully apparent from the following detailed description, the appended claims and the accompanying drawings and figures.

BRIEF DESCRIPTION OF THE DRAWINGS

A further understanding of the various embodiments may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Figure 1A:
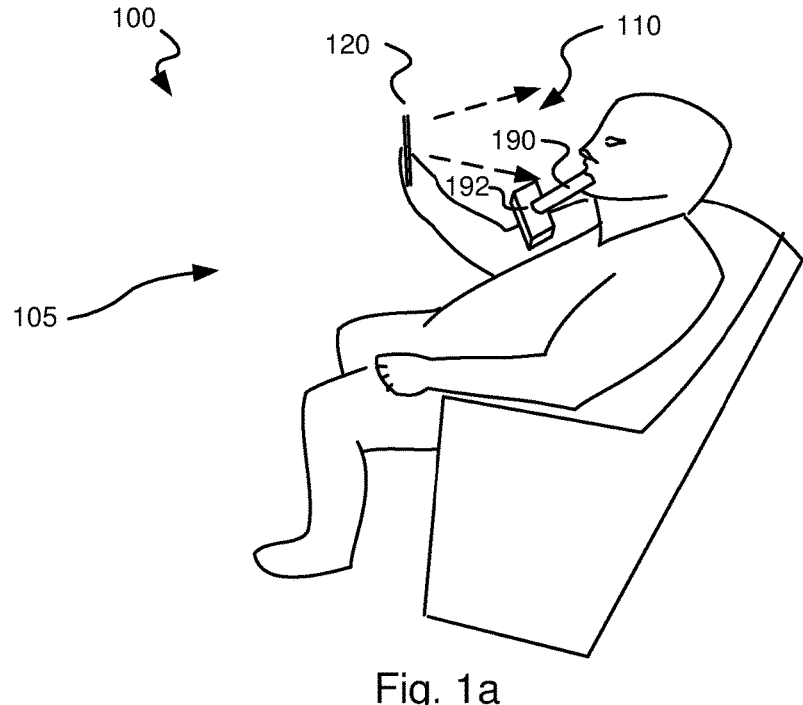
FIG. 1A shows a scenario where a monitored individual is using an impairment detection device while an image is taken of the monitored individual using the impairment detection device.

Various embodiments provide systems and methods for identifying impairment using measurement devices and trained models. Embodiments discussed herein provide systems, methods, and/or devices that enable remote impairment testing that does not require a human monitor to be present or physically near the individual being monitored. Such an ability is an improvement.

Some embodiments provide systems for determining proper use of a breath tester. Such systems include: a camera; a breath tube; one or more processors configured to receive an image from the camera of a monitored individual blowing into the breath tube; and a non-transient computer readable medium coupled to the one or more processors. The non-transient computer readable medium has stored therein instructions which when executed by the one or more processors, causes the one or more processors to: apply an interference classification model to the image to yield a probability that the monitored individual is interfering with gas flowing from the monitored individual's mouth via the breath tube; indicate interference when the probability exceeds a first threshold; and indicate no interference when the probability is less than a second threshold.

In some instances of the aforementioned embodiments, the non-transient computer readable medium further has stored therein instructions which when executed by the one or more processors, causes the one or more processors to forward the image to a user for classification when the probability is both less than the first threshold and greater than the second threshold. In various instances of the aforementioned embodiments, the non-transient computer readable medium further has stored therein instructions which when executed by the one or more processors, causes the one or more processors to request that the monitored individual adjust the breath tube when the probability is both less than the first threshold and greater than the second threshold.

In various instances of the aforementioned embodiments, the non-transient computer readable medium further has stored therein instructions which when executed by the one or more processors, causes the one or more processors to perform an impairment test of the monitored individual when the probability is less than the second threshold, wherein the impairment test is based upon a breath sample of the monitored individual received via the breath tube. In some such instances, the non-transient computer readable medium further has stored therein instructions which when executed by the one or more processors, causes the one or more processors to report an impairment result of the impairment test to a recipient device apart from the one or more processors. In various such instances of the aforementioned embodiments, the impairment test includes at least one of: a breath based drug impairment test, or a breath based alcohol impairment test.

In some instances of the aforementioned embodiments, the interference classification model is a machine learning model trained using at least one hundred images that have each been classified as exhibiting interference or not exhibiting interference. In some such instances, the at least one hundred images depict at least ten different individuals undergoing a breath based impairment test.

Other embodiments provide methods for determining proper application of a breath based impairment test. Such methods include: capturing an image using a camera of a monitored individual blowing into a breath tube; applying, by a hardware processing system, an interference classification model to the image to yield a probability that the monitored individual is interfering with gas flowing from the monitored individual's mouth via the breath tube; comparing, by the hardware processing system, the probability with a first threshold and generating an indication of interference when the probability exceeds the first threshold; and comparing, by the processor, the probability with a second threshold comparing, by the hardware processing system, the probability with a first threshold and generating an indication of no interference when the probability is less than the second threshold. In some embodiments only a single image is used. In such embodiments, the single image may be extracted from, for example, a stream of images received from a camera. In other embodiments, multiple different images are used to evaluate. In such embodiments, the multiple images may be extracted from the same stream of images received from a camera.

Yet other embodiments provide non-transient computer readable media that have stored therein instructions, which when executed by a hardware processing system, cause the hardware processing system to: receive an image from a camera, wherein the image shows a monitored individual blowing into a breath tube; apply an interference classification model to the image to yield a probability that the monitored individual is interfering with gas flowing from the monitored individual's mouth via the breath tube; compare the probability with a first threshold and generating an indication of interference when the probability exceeds the first threshold; compare the probability with a second threshold and generating an indication of no interference when the probability is less than the second threshold; perform an impairment test of the monitored individual based at least in part on the indication of no interference and a breath sample of the monitored individual received via the breath tube; and report an impairment result of the impairment test to a recipient device apart from the one or more processors.

Some embodiments provide systems for detecting drug based impairment. Such systems include: a breath input device; a breath sensor configured to receive a breath sample of an individual via the breath input device and to provide a sample value corresponding to the breath sample; one or more processors; and a non-transient computer readable medium coupled to the one or more processors. The non-transient computer readable medium has stored therein instructions which when executed by the one or more processors, causes the one or more processors to: receive the sample value; apply a drug impairment model to the sample data to yield a probability that the individual is impaired; indicate a likelihood of impairment when the probability exceeds a first threshold; and indicate no impairment when the probability is less than a second threshold.

In some instances of the aforementioned embodiments where the probability is a first probability, the system further include a camera. In such systems, the non-transient computer readable medium further has stored therein instructions which when executed by the one or more processors, causes the one or more processors to: receive an image captured by the camera of the individual blowing into the breath input device; apply an interference classification model to the image to yield a second probability that the individual is interfering with gas flowing from the mouth of the individual via the breath input device; indicate a likelihood of interference when the second probability exceeds a third threshold; and cause a request to be sent to the individual to modify use of the breath input device when the second probability exceeds a third threshold.

In various instances of the aforementioned embodiments where the system further includes a camera, the non-transient computer readable medium further has stored therein instructions which when executed by the one or more processors, causes the one or more processors to: receive a facial image of the individual captured by the camera; and perform a facial image based impairment test using the facial image. In some instances of the aforementioned embodiments where the sample value is a first sample value and the breath sensor is further configured to provide a second sample value corresponding to the breath sample, the non-transient computer readable medium further has stored therein instructions which when executed by the one or more processors, causes the one or more processors to perform a breath alcohol based impairment test using the second sample value.

In some instances of the aforementioned embodiments, the sample value is a level of a defined volatile organic compound. In some such instances, the defined volatile organic compound is one of: a volatile organic compound indicative of methamphetamine, a volatile organic compound indicative of marijuana, a volatile organic compound indicative of cocaine, or a volatile organic compound indicative of heroin. In various instances of the aforementioned embodiments, the non-transient computer readable medium further has stored therein instructions which when executed by the one or more processors, causes the one or more processors to forward the sample value to a user for classification when the probability is both less than the first threshold and greater than the second threshold. While the described embodiment discusses a sample value that is a level of a defined volatile organic compound, in other embodiments multiple sample values may be generated from the same breath sample with each of the multiple sample values corresponding different defined volatile organic compounds. As such, the multiple sample values may be indicative of a combination of defined organic compounds including, but not limited to, a volatile organic compound indicative of methamphetamine and a volatile organic compound indicative of marijuana, a volatile organic compound indicative of methamphetamine and a volatile organic compound indicative of cocaine, a volatile organic compound indicative of methamphetamine and a volatile organic compound indicative of heroin, a volatile organic compound indicative of marijuana and a volatile organic compound indicative of cocaine, a volatile organic compound indicative of marijuana and a volatile organic compound indicative of heroin, or a volatile organic compound indicative of cocaine and a volatile organic compound indicative of heroin. Extending the example further, the multiple sample values may be indicative of a combination of three more defined organic compounds. Based upon the disclosure provided herein, one of ordinary skill in the art will recognize a variety of volatile organic compounds and/or combinations thereof that may be processed in accordance with different embodiments.

In various instances of the aforementioned embodiments, the non-transient computer readable medium further has stored therein instructions which when executed by the one or more processors, causes the one or more processors to cause a request to be sent to the individual to perform an additional impairment test. In some such instances, the additional impairment test is one of: a voice based impairment test, or a movement based impairment test. In some instances of the aforementioned embodiments, the non-transient computer readable medium further has stored therein instructions which when executed by the one or more processors, causes the one or more processors to report the likelihood of impairment to a recipient device apart from the one or more processors. In various instances of the aforementioned embodiments, the drug impairment model is a machine learning model trained using breath samples that have each been classified as exhibiting a defined volatile organic compound corresponding a controlled substance.

In some instances of the aforementioned embodiments where the sample value is a first sample value and the breath sensor is further configured to provide a second sample value corresponding to the breath sample, the non-transient computer readable medium further has stored therein instructions which when executed by the one or more processors, causes the one or more processors to perform a breath alcohol based impairment test using the second sample value. Ion various instances of the aforementioned embodiments, the non-transient computer readable medium further has stored therein instructions which when executed by the one or more processors, causes the one or more processors to perform an additional impairment test when the probability is both less than the first threshold and greater than the second threshold. In such instances, the additional impairment test is one of: a voice based impairment test, a movement based impairment test, a facial image based impairment test, or a breath alcohol based impairment test.

Other embodiments provide methods for detecting use of a controlled substance. Such methods include: processing, by a breath sensor, a breath sample received from an individual; providing, by the breath sensor, a sample value corresponding to the breath sample; applying, by a processor, a drug impairment model to the sample data to yield a probability that the individual is impaired; indicating, by the processor, a likelihood of usage when the probability exceeds a first threshold; and indicating, by the processor, no usage when the probability is less than a second threshold.

Yet other embodiments provide non-transient computer readable media has stored therein instructions, which when executed by a hardware processing system cause the hardware processing system to: receive a sample value, wherein the sample value is generated by a breath sensor based upon a breath sample received from an individual via a breath input device; apply a drug impairment model to the sample data to yield a probability that the individual is impaired; indicate a likelihood of impairment when the probability exceeds a first threshold; and indicate no impairment when the probability is less than a second threshold.

Some embodiments provide systems for detecting alcohol based impairment. Such systems include: a camera; a breath input device; a breath sensor configured to receive a breath sample of an individual via the breath input device and to generate an alcohol level based upon the breath sample; one or more processors; and a non-transient computer readable medium coupled to the one or more processors. The non-transient computer readable medium has stored therein instructions which when executed by the one or more processors, causes the one or more processors to: receive an image captured by the camera of the individual blowing into the breath input device; apply an interference classification model to the image to yield a probability that the individual is interfering with gas flowing from the mouth of the individual via the breath input device; indicate a likelihood of no interference when the probability is less than a threshold; and based at least in part on the likelihood of no interference, indicate the alcohol level as reliable.

In some instances of the aforementioned embodiments, the non-transient computer readable medium further has stored therein instructions which when executed by the one or more processors, causes the one or more processors to cause a request to be sent to the individual to perform an additional impairment test. In some such instances, the additional impairment test is selected from a group consisting of: a voice based impairment test, and a movement based impairment test.

In various instances of the aforementioned embodiments where the threshold is a first threshold, the non-transient computer readable medium further has stored therein instructions which when executed by the one or more processors, causes the one or more processors to: indicate a likelihood of interference when the probability exceeds a second threshold; and cause a request to be sent to the individual to modify use of the breath input device when the probability exceeds the second threshold. In some instances of the aforementioned embodiments, the non-transient computer readable medium further has stored therein instructions which when executed by the one or more processors, causes the one or more processors to: receive a facial image of the individual captured by the camera; and perform a facial image based impairment test using the facial image. In some embodiments of the aforementioned embodiments, the non-transient computer readable medium further has stored therein instructions which when executed by the one or more processors, causes the one or more processors to report the likelihood of impairment to a recipient device apart from the one or more processors.

In various instances of the aforementioned embodiments, the interference classification model is a machine learning model trained using at least one hundred images that have each been classified as exhibiting interference or not exhibiting interference. In some such instances, the at least one hundred images depict at least ten different individuals undergoing a breath based impairment test.

In some instances of the aforementioned embodiments, the breath sensor is further configured to provide a sample value corresponding to the breath sample, and the non-transient computer readable medium further has stored therein instructions which when executed by the one or more processors, causes the one or more processors to perform a drug based impairment test using the sample value. In some such instances, the sample value is a level of a defined volatile organic compound.

Other embodiments provide methods for detecting use of a controlled substance. Such methods include: receiving, by a processor, an image captured by a camera of an individual blowing into a breath input device; processing, by a breath sensor, a breath sample derived from the individual via a breath input device to yield an alcohol level in the breath sample; applying, by the processor, an interference classification model to the image to yield a probability that the individual is interfering with gas flowing from the mouth of the individual via the breath input device; indicating, by the processor, a likelihood of no interference when the probability is less than a threshold; and based at least in part on the likelihood of no interference, indicating the alcohol level as reliable.

Yet other embodiments provide non-transient computer readable media that have stored therein instructions, which when executed by a hardware processing system cause the hardware processing system to: receive an image captured by a camera of an individual blowing into a breath input device; receive an alcohol level from a breath sensor, wherein the alcohol level is generated by the breath sensor based upon a breath sample derived from the individual via a breath input device; apply an interference classification model to the image to yield a probability that the individual is interfering with gas flowing from the mouth of the individual via the breath input device; indicate the processor, a likelihood of no interference when the probability is less than a threshold; and based at least in part on the likelihood of no interference, indicating the alcohol level as reliable.

Some embodiments provide systems for detecting impairment based upon voice data. The system includes: a a microphone configured to receive audio information from an individual and to provide a voice data corresponding to the audio information; one or more processors; and a non-transient computer readable medium coupled to the one or more processors. The non-transient computer readable medium has stored therein instructions which when executed by the one or more processors, causes the one or more processors to: receive the voice data from the microphone; apply a voice impairment model to the voice data to yield a probability that the individual is impaired; indicate a likelihood of impairment based at least in part on a determination that the probability exceeds a first threshold; and indicate no impairment when the probability is less than a second threshold.

In some instances of the aforementioned embodiments, the non-transient computer readable medium further has stored therein instructions which when executed by the one or more processors, causes the one or more processors to apply an anomaly detection model to the voice data to yield an individual anomaly output. The likelihood of impairment is indicated when both the individual anomaly output indicates that the voice data is an anomaly for the individual and the probability exceeds the first threshold. In some cases, the anomaly detection model is trained using at least ten instances of voice data derived from the individual.

In various instances of the aforementioned embodiments, the voice impairment model is a machine learning model trained using at least one hundred instances of voice data. In some such cases, the at least one hundred instances of voice data correspond to at least ten different individuals undergoing a voice based impairment test.

In some instances of the aforementioned embodiments, the non-transient computer readable medium further having stored therein instructions which when executed by the one or more processors, causes the one or more processors to cause a request to be sent to the individual to perform an additional impairment test. In some such cases the additional impairment test is one or more of: a facial image based impairment test, or a movement based impairment test.

In various instances of the aforementioned embodiments, the non-transient computer readable medium further having stored therein instructions which when executed by the one or more processors, causes the one or more processors to forward the voice data to a user for classification when the probability is both less than the first threshold and greater than the second threshold. In some instances of the aforementioned embodiments, the non-transient computer readable medium further having stored therein instructions which when executed by the one or more processors, causes the one or more processors to report the likelihood of impairment to a recipient device apart from the one or more processors.

Other embodiments provide methods for detecting impairment based upon voice data. The methods include: receiving, by a processor, voice data captured by a microphone; applying, by the processor, a voice impairment model to the voice data to yield a probability that the individual is impaired; indicating, by the processor, a likelihood of impairment based at least in part on a determination that the probability exceeds a first threshold; and indicating, by the processor, no impairment when the probability is less than a second threshold.

Yet other embodiments provide non-transient computer readable media having stored therein instructions, which when executed by a hardware processing system cause the hardware processing system to: receive a voice data from the microphone, where the voice data corresponds to a voice of an individual; apply a voice impairment model to the voice data to yield a probability that the individual is impaired, where the voice impairment model is a machine learning model trained using at least one hundred instances of voice data and the at least one hundred instances of voice data correspond to at least ten different individuals undergoing a voice based impairment test; indicate a likelihood of impairment based at least in part on a determination that the probability exceeds a first threshold; and indicate no impairment when the probability is less than a second threshold.

Some embodiments provide systems for detecting impairment based upon movement. Such systems include: a movement sensor configured to receive movement information about a user detached monitor device; one or more processors; and a non-transient computer readable medium coupled to the one or more processors. The non-transient computer readable medium has stored therein instructions which when executed by the one or more processors, causes the one or more processors to: receive the movement information from the movement sensor; apply a movement impairment model to the movement information to yield a probability that the individual is impaired; indicate a likelihood of impairment based at least in part on a determination that the probability exceeds a first threshold; and indicate no impairment when the probability is less than a second threshold.

In some instances of the aforementioned embodiments, the systems further include a camera. In some such instances, the non-transient computer readable medium further has stored therein instructions which when executed by the one or more processors, causes the one or more processors to: receive an image of surroundings of the individual; and based upon the image showing one or more physical supports around the individual, cause a request for the individual to move to another location. In other such instances, the non-transient computer readable medium further has stored therein instructions which when executed by the one or more processors, causes the one or more processors to receive an image of surroundings of the individual. Indicating no impairment is based at least in part on the image showing the individual located away from a physical support. In various instances of the aforementioned embodiments, the movement impairment model is a machine learning model trained using at least one hundred instances of movement information data. In some such instances, the at least one hundred instances of movement information correspond to at least ten different individuals undergoing a movement based impairment test.

In various instances of the aforementioned embodiments, the systems further include a camera and a display. In some such instances, the non-transient computer readable medium further has stored therein instructions which when executed by the one or more processors, causes the one or more processors to: receive a face image of the individual indicating the individual is watching the display; and cause a video stream to play on the display. Indicating no impairment is based at least in part on the face image of the individual indicating the individual is watching the display.

In some instances of the aforementioned embodiments, the non-transient computer readable medium further has stored therein instructions which when executed by the one or more processors, causes the one or more processors to compare the movement information with a movement threshold. Indicating no impairment is based at least in part on the movement information being greater than the movement threshold. In various instances of the aforementioned embodiments, the non-transient computer readable medium further has stored therein instructions which when executed by the one or more processors, causes the one or more processors to cause a request to be sent to the individual to perform an additional impairment test. In some such instances, the additional impairment test is at least one of: a facial image based impairment test, and/or a voice based impairment test.

In some instances of the aforementioned embodiments, the non-transient computer readable medium further has stored therein instructions which when executed by the one or more processors, causes the one or more processors to forward the movement information to a user for classification when the probability is both less than the first threshold and greater than the second threshold. In various instances of the aforementioned embodiments, the non-transient computer readable medium further has stored therein instructions which when executed by the one or more processors, causes the one or more processors to report the likelihood of impairment to a recipient device apart from the one or more processors.

Other embodiments provide methods for detecting impairment based upon movement information. Such methods include: receiving, by a processor, movement information from a movement sensor included in a user detached monitor device; applying, by the processor, a movement impairment model to the movement information to yield a probability that the individual is impaired; indicating, by the processor, a likelihood of impairment based at least in part on a determination that the probability exceeds a first threshold; and indicating, by the processor, no impairment when the probability is less than a second threshold.

Yet other embodiments provide non-transient computer readable media having stored therein instructions, which when executed by a hardware processing system cause the hardware processing system to: receive movement information from a movement sensor; apply a movement impairment model to the movement information to yield a probability that the individual is impaired; indicate a likelihood of impairment based at least in part on a determination that the probability exceeds a first threshold; and indicate no impairment when the probability is less than a second threshold. The movement impairment model is a machine learning model trained using at least one hundred instances of movement information data, and the at least one hundred instances of movement information correspond to at least ten different individuals undergoing a movement based impairment test.

Some embodiments provide systems for detecting impairment based upon facial image. Such systems include: a camera configured to capture a facial image of an individual; one or more processors; and a non-transient computer readable medium coupled to the one or more processors. The non-transient computer readable medium has stored therein instructions which when executed by the one or more processors, causes the one or more processors to: receive the facial image of the individual from the camera; apply a facial image impairment model to the facial image to yield a probability that the individual is impaired; indicate a likelihood of impairment based at least in part on a determination that the probability exceeds a first threshold; and indicate no impairment when the probability is less than a second threshold.

In some instances of the aforementioned embodiments, the non-transient computer readable medium further has stored therein instructions which when executed by the one or more processors, causes the one or more processors to: apply an anomaly detection model to the facial image to yield an individual anomaly output; and wherein the likelihood of impairment is indicated when both the individual anomaly output indicates that the facial image is an anomaly for the individual and the probability exceeds the first threshold. In some such instances, the anomaly detection model is trained using at least ten instances of facial images of the individual.

In various instances of the aforementioned embodiments, the non-transient computer readable medium further has stored therein instructions which when executed by the one or more processors, causes the one or more processors to cause a request to be sent to the individual to perform an additional impairment test. In some such instances, the additional impairment test includes at least one of: a voice based impairment test, and a movement based impairment test.

In some instances of the aforementioned embodiments, the non-transient computer readable medium further has stored therein instructions which when executed by the one or more processors, causes the one or more processors to forward the facial image to a user for classification when the probability is both less than the first threshold and greater than the second threshold. In various instances of the aforementioned embodiments, the non-transient computer readable medium further has stored therein instructions which when executed by the one or more processors, causes the one or more processors to report the likelihood of impairment to a recipient device apart from the one or more processors.

In various instances of the aforementioned embodiments, the facial image impairment model is a machine learning model trained using at least one hundred facial images. In some such instances, the at least one hundred facial images correspond to at least ten different individuals undergoing a facial image based impairment test.

Other embodiments provide methods for detecting impairment based upon facial images. Such methods include: receiving, by a processor, a facial image of an individual from a camera; applying, by the processor, a facial image impairment model to the facial image to yield a probability that the individual is impaired; indicating, by the processor, a likelihood of impairment based at least in part on a determination that the probability exceeds a first threshold; and indicating, by the processor, no impairment when the probability is less than a second threshold. The facial image impairment model is a machine learning model trained using at least one hundred facial images, and the at least one hundred facial images correspond to at least ten different individuals undergoing a facial image based impairment test.

Yet other embodiments provide non-transient computer readable media having stored therein instructions, which when executed by a hardware processing system cause the hardware processing system to: receive a facial image of an individual from a camera; apply a facial image impairment model to the facial image to yield a probability that the individual is impaired; indicate a likelihood of impairment based at least in part on a determination that the probability exceeds a first threshold; and indicate no impairment when the probability is less than a second threshold. The facial image impairment model is a machine learning model trained using at least one hundred facial images, and the at least one hundred facial images correspond to at least ten different individuals undergoing a facial image based impairment test FIG. 1A shows a scenario where a monitored individual 105 is using breath based impairment detection device 192 including a breath tube 190 that can be inserted into the mouth of monitored individual 105 while an image is taken of monitored individual 105 using a user detached monitor device 120 having a camera with a field of view 110. Of note, while some embodiments are discussed herein as using a camera on one device to take an image and the impairment analysis tools from another device to discern impairment, other embodiments may use a unified device where a camera is included in breath based impairment detection device 192. In yet other embodiments, breath based impairment detection device 192 and/or user detached monitor device 120 are capable of independently determining impairment based upon one or more classes of data received about monitored individual. In yet further embodiments, breath based impairment detection device 192 and/or user detached monitor device 120 are capable of receiving one or more classes of data received about monitored individual, and providing the received data to a central monitoring system (not shown) where the transferred information is processed to yield an indication that monitored individual is impaired or not. Based upon the disclosure provided herein, one of ordinary skill in the art will recognize a variety of combinations of hardware that may be used to perform the impairment analysis in accordance with different embodiments.

One or more impairment determinations and/or tamper determinations are performed using a model trained to assess impairment and/or tampering based upon a respective one of the received classes of data about monitored individual. In some instances, respective ones of the trained models are trained using data specific to monitored individual 105 and in other instances other ones of the trained models are trained using generic data from many individuals.

As an example, an interference model may be used that determines whether breath tube 190 is properly inserted into the mouth of monitored individual 105. This model may be trained using data from multiple individuals. Once it is established that breath tube 190 is properly inserted, a standard breathalyzer test may be performed to determine the blood alcohol level of monitored individual and thereby the alcohol based impairment of monitored individual 105.

As another example, the previously discussed interference model may be used to determine whether breath tube 190 is properly inserted into the mouth of monitored individual 105. Again, this model may be trained using data from multiple individuals. Once it is established that breath tube 190 is properly inserted, breath data received from monitored individual 105 is analyzed by a drug impairment model to determine a likelihood that monitored individual 105 is impaired. This drug impairment model may be trained using data from multiple individuals.

As yet another example, voice data from monitored individual 105 may be received. A supervised anomaly model is applied to the received voice data to determine if the voice data is within an expected range of voice data from monitored individual 105. This supervised anomaly model is trained using data specific to monitored individual 105. Where an anomaly is determined, the voice data is processed by a voice impairment model to determine a likelihood that monitored individual 105 is impaired. This voice impairment model may be trained using data from multiple individuals.

As an additional example, movement data from monitored individual 105 may be received. A supervised anomaly model is applied to the received movement data to determine if the movement data is within an expected range of movement data from monitored individual 105. This supervised anomaly model is trained using data specific to monitored individual 105. Where an anomaly is determined, the movement data is processed by a movement based impairment model to determine a likelihood that monitored individual 105 is impaired. This movement based impairment model may be trained using data from multiple individuals.

As yet a further example, facial image data from monitored individual 105 may be received. A supervised anomaly model is applied to the received facial image data to determine if the facial image data is within an expected range of facial image data from monitored individual 105. This supervised anomaly model is trained using data specific to monitored individual 105. Where an anomaly is determined, the facial image data is processed by a facial image based impairment model to determine a likelihood that monitored individual 105 is impaired. This facial image based impairment model may be trained using data from multiple individuals.

Figure 1B:
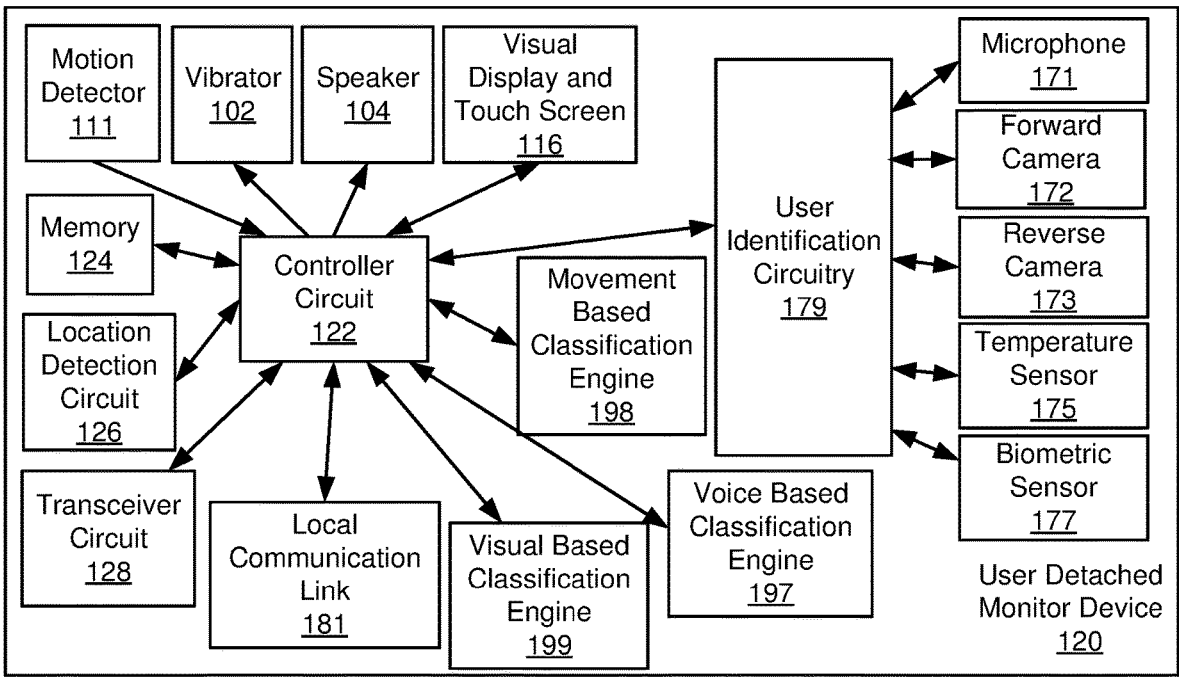
FIG. 1B is a block diagram of a user detached monitor device including various sensors and processors usable in accordance with one or more embodiments.

FIG. 1B is a block diagram of a user detached monitor device 120 including a forward camera 172 is shown that is usable in accordance with one or more embodiments. User detached monitor device 120 includes wireless transceiver circuitry 128 that is capable of sending and receiving information via wireless link (not shown) to/from wide area wireless network (not shown). Wireless transceiver circuitry 128 may be any circuitry, integrated circuit, and/or processor or controller capable of supporting wireless communication. Such wireless communication may include, but is not limited to, cellular telephone communication, Internet communication via a Wi-Fi access point, or both. In addition, user detached monitor device 120 includes a vibrator 102, a speaker 104, and a visual display and touch screen 116. In some cases, at scheduled times a monitored individual associated with user detached monitor device 120 is alerted of a need to check-in. The schedule of check-in times may be downloaded to a memory 124 by central monitoring station 160 via wireless link 133. The monitored individual may be alerted by one or more of: a visual prompt via visual display and touch screen 116, an audio prompt via speaker 114, and a tactile prompt via vibrator 112. Each of vibrator 112, speaker 114, and visual display and touch screen 116 is communicatively coupled to memory 124 and/or a controller circuit 122 for controlling the operations thereof. In some cases, controller circuit 122 includes a processor. In various cases, controller circuit 122 is part of an integrated circuit. In one or more cases, memory 124 is included in an integrated circuit with controller circuit 122. In various cases, memory 124 may include non-transient instructions (e.g., software or firmware-based based instructions) executable by controller circuit 122 to perform and/or enable various functions associated with user detached monitor device 120. In some embodiments, controller circuit 122 executes instructions to perform one or more of the impairment determination processes discussed below.

A visual prompt may include, but is not limited to, text, images and/or a combination thereof, or a series of such visual prompts. An audio prompt may include, but is not limited to, one or more different audio prompts, or a series thereof. Each prompt may be stored in memory 124 and retrieved in accordance with the schedule that is also maintained in memory 124. In some embodiments, alerting the monitored individual involves a prompt that includes an e-mail or text message generated by a central monitoring station (e.g. a server supported website that is not shown) and transmitted to the e-mail account or cellular phone number corresponding to user detached monitor device 120. In particular embodiments, such a prompt may include a 'post' on the user's 'wall,' 'feed,' or other social networking privilege. In some embodiments, the prompt may comprise an automated or live phone call to the monitored individual.

User detached monitor device 120 further includes user identification circuitry 179 capable of gathering user identification information from one or more of a microphone 171 (i.e., a voice data class), a forward and/or reverse camera 172, 173 (i.e., an image data class), a temperature sensor 175 (i.e., an ambient temperature data class), and/or a biometric sensor 177 (i.e., a biometric data class). In some cases, user identification circuitry 179 is incorporated in an integrated circuit with controller circuit 122. Microphone 171 is capable of accurately capturing the sound of a monitored individual's voice, forward and/or reverse cameras 172, 173 are each capable of accurately capturing images including, for example, an image of the monitored individual's face, temperature sensor 175 is capable of accurately capturing an ambient temperature around user detached monitor device 120, and biometric sensor 177 is capable of accurately capturing biometric data about the monitored individual including, but not limited to, a thumb print, a retinal scan, or a breath-based alcohol measurement. Based upon the disclosure provided herein, one of ordinary skill in the art will recognize a variety of biometric data and corresponding sensors that may be used in relation to different embodiments. Under the direction of control circuitry 122, user identification circuitry 179 assembles one or more elements of data gathered by microphone 171, a camera 173, a temperature sensor 175, and/or a biometric sensor 177 into a user identification package which is forwarded to central monitoring station 160 via wireless transceiver circuitry 128. User detached monitor device 120 additionally includes a motion detector 111 operable to discern whether user detached monitor device is moving, and by implication whether a monitored individual holding user detached monitor device 120 is moving. In some cases, motion detector 120 includes an accelerometer circuit. Based upon the disclosure provided herein, one of ordinary skill in the art will recognize various circuits and/or sensors capable of indicating that user detached monitor device is moving that may be used in relation to different embodiments.

User detached monitor device 120 additionally includes location detection circuitry 126. Location detection circuitry 126 may include one or more of, a GPS processing circuit capable of fixing a location of user detached monitor device 120 using GPS data, a WiFi based location circuit capable of fixing a location of user detached monitor device 120 using contact information with one or more WiFi access points, and/or a cell tower triangulation processing circuit capable of fixing a location of user detached monitor device 120 using cell tower triangulation data. A local communication link 181 controls communication between user detached monitor device 120 and breath based impairment detection device 192. In some embodiments, local communication link 181 supports a Bluetooth™ communication protocol and is capable of both receiving information from breath based impairment detection device 192 and transmitting information to breath based impairment detection device 192. In other embodiments, local communication link 181 supports a Wi-Fi communication protocol and is capable of both receiving information from breath based impairment detection device 192 and transmitting information to breath based impairment detection device 192. In some cases, local communication link 181 supports communication in only a receive or transmit direction. Based upon the disclosure provided herein, one of ordinary skill in the art will recognize a variety of communication protocols and information transfer directions that may be supported by local communication link 181 in accordance with different embodiments.

Additionally, user detached monitor device 120 includes a voice based classification engine 197, a movement based classification engine 198, and a visual based classification engine 199. Voice based classification engine 197 is configured to apply voice data derived from microphone 171 to both an anomaly determination model and a voice based impairment detection model to determine an impairment status of the monitored individual. In some cases, voice based classification engine 197 performs processes similar to those discussed below in relation to FIG. 14.

Movement based classification engine 198 is configured to apply movement information derived from motion detector 111 to both an anomaly determination model and a movement based impairment detection model to determine an impairment status of the monitored individual. In some cases, movement based classification engine 197 performs processes similar to those discussed below in relation to FIG. 15.

Visual based classification engine 199 is configured to apply facial image data derived from forward camera 172 to both an anomaly determination model and a facial image based impairment detection model to determine an impairment status of the monitored individual. In some cases, facial image based classification engine 199 performs processes similar to those discussed below in relation to FIG. 16. Additionally, visual based classification engine 199 is to apply visual image data derived from forward camera 172 to an interference classification model to determine if a monitored individual is attempting to tamper with a breath based test.

Figure 1C:
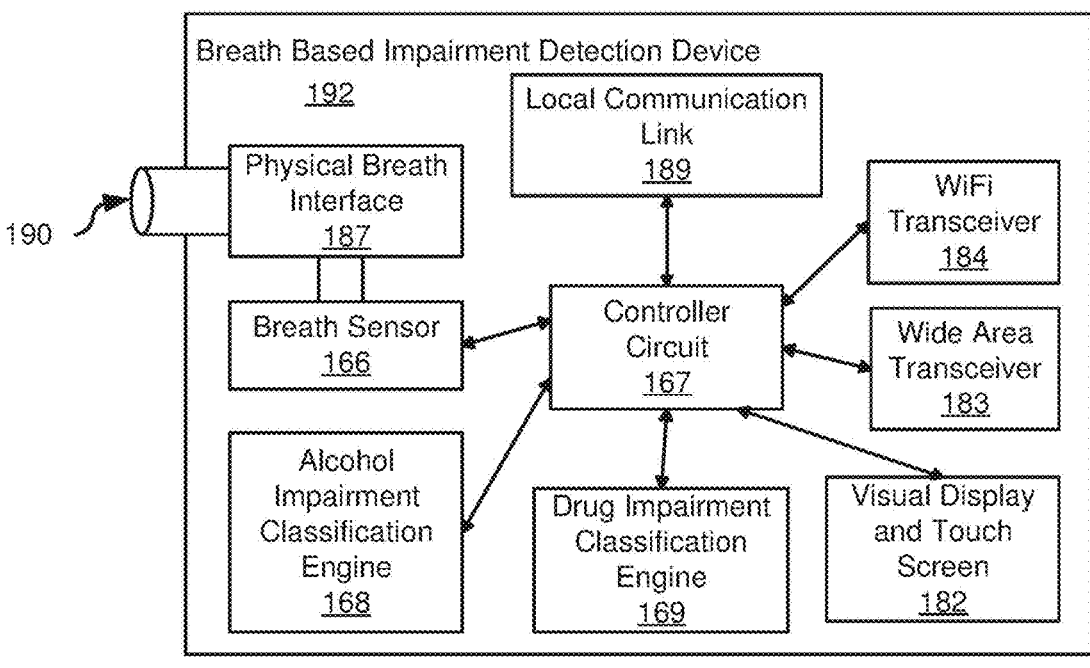
FIG. 1C is a block diagram of an impairment detection device capable of receiving input from a monitored individual and generating an impairment result based upon the input from the monitored individual and transferring the impairment result to a central monitor via a transceiver that is usable in relation to various embodiments.

FIG. 1C is a block diagram of breath based impairment detection device 192 capable of receiving input from monitored individual 105 via a tube 190 at a breath sensor 166, and generating an impairment result by one or both of an alcohol impairment classification engine 168 and a drug impairment classification engine 169, with each under control of a controller circuit 167. Breath sensor 166 may be, but is not limited to: a single test sensor capable of providing a single defined output value (e.g., alcohol value or a specific volatile organic compound (VOC) level), a multiple test sensor capable of providing multiple defined output values (e.g., alcohol value, a first specific volatile organic compound (VOC) level, and a second specific VOC level), and/or a combination of two or more single test sensors each configured to provide different defined output values. Instructions can be received via a wide area transceiver 183 communicating via a wide area network (not shown) or via a WiFi transceiver 184 communicating via a WiFi network (not shown). Similarly, results from alcohol impairment classification engine 168 and/or drug impairment classification engine 169 can be communicated via wide area transceiver 183 communicating or via WiFi transceiver 184.

A local communication link 189 controls communication between breath based impairment detection device 192 and user detached monitor device 120. In some embodiments, local communication link 189 supports a Bluetooth™ communication protocol and is capable of both receiving information from user detached monitor device 120 and transmitting information to user detached monitor device 120. In other embodiments, local communication link 189 supports a Wi-Fi communication protocol and is capable of both receiving information from user detached monitor device 120 and transmitting information to user detached monitor device 120. In some cases, local communication link 189 supports communication in only a receive or a transmit direction. Based upon the disclosure provided herein, one of ordinary skill in the art will recognize a variety of communication protocols and information transfer directions that may be supported by local communication link 189 in accordance with different embodiments.

A physical breath interface 187 includes the structure to connect to breath tube 190, and to transmit breath received from breath tube 190 to a breath sensor 166. Breath sensor 166 may be any sensor or set of sensors known in the art that are capable of detecting volatile organic compounds (VCOs) and/or alcohol within a breath sample. Based upon the disclosure provided herein, one of ordinary skill in the art will recognize a variety of sensors and/or combinations of sensors that may be used in relation to different embodiments. Breath sensor 166 provides communications indicating the level of VCOs and/or alcohol sensed in a breath received via physical breath interface.

The VCO information along with information from visual based classification engine 199 received via local communication link 189 and indicating any tampering with the breath based test are provided to drug impairment classification engine 169. In some cases, drug impairment classification engine 169 performs various processes discussed below in relation to FIGS. 17a-17b.

The alcohol information along with information from visual based classification engine 199 received via local communication link 189 and indicating any tampering with the breath based test are provided to alcohol impairment classification engine 168. In some cases, alcohol impairment classification engine 168 performs various processes discussed below in relation to FIG. 16.

Breath based impairment detection device 192 also includes a visual display and touch screen 182. In some cases, at scheduled times a monitored individual associated with user Breath based impairment detection device 192 is alerted of a need to check-in. The schedule of check-in times may be downloaded to a memory (not shown) included in breath based impairment detection device 192 by a central monitoring station (not shown). The monitored individual may be alerted by one or more of: a visual prompt via visual display and touch screen 182. In some cases, controller circuit 167 includes a processor. In various cases, controller circuit 167 is part of an integrated circuit. In one or more cases, the memory is included in an integrated circuit with controller circuit 167. In various cases, the memory may include non-transient instructions (e.g., software or firmware-based based instructions) executable by controller circuit 167 to perform and/or enable various functions associated with breath based impairment detection device 192. In some embodiments, controller circuit 167 executes instructions to perform one or more of the impairment determination processes discussed below.

Figure 1D:
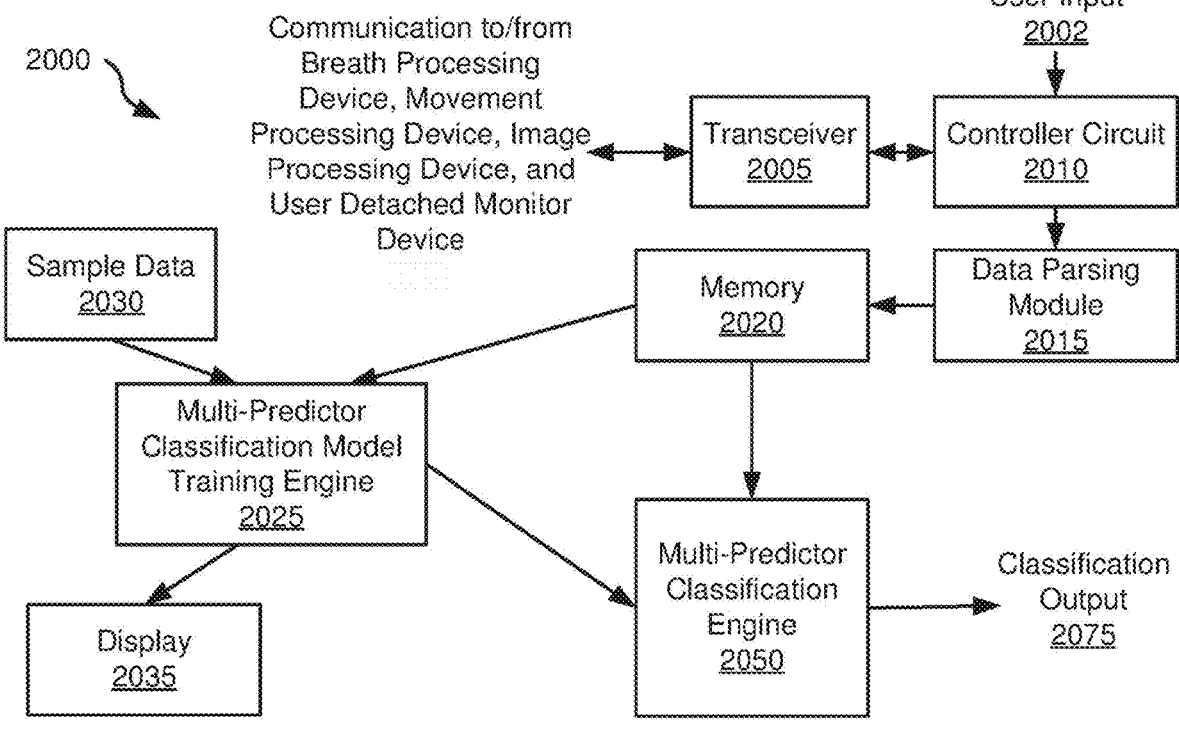
FIG. 1D is a block diagram of a central monitoring system capable of communicating with one or both of a user detached monitoring device and/or an impairment detection device and performing multi-predictor impairment classification in accordance with various embodiments.

Turning to FIG. 1D, a block diagram is shown of a central monitoring system 2000 capable of communicating with one or both of user detached monitor device 120 and/or breath based impairment detection device 192, and performing multi-predictor impairment classification in accordance with various embodiments. As shown, central monitoring system 2000 includes a transceiver 2005 capable of receiving and sending communications to/from various processing devices including, but not limited to, user detached monitor device 120 and/or breath based impairment detection device 192.

The data transmitted via transceiver 2005 is provided from a controller circuit 2010, and the data received via transceiver 2005 is provided to controller circuit 2010. In some cases, controller circuit 2010 includes a processor. In various cases, controller circuit 2010 is part of an integrated circuit. In one or more cases, memory is included in an integrated circuit with controller circuit 2010. In various cases, the memory may include non-transient instructions (e.g., software or firmware-based based instructions) executable by controller circuit 2010 to perform and/or enable various functions associated with central monitoring system. In some embodiments, controller circuit 2010 executes instructions to perform one or more of the impairment determination processes discussed below. Controller circuit 2010 is communicably coupled to a memory 2020 where data may be stored and from which data may be retrieved.

A data parsing module 2015 extracts data received via transceiver 2005 to yield various classes of data (e.g., a voice data class, an image data class, an ambient temperature data class, a biometric data class, a VOC data class, a movement data class, a voice data class, and/or an alcohol data class). Each of the different data classes may be stored in different locations in memory 2020 of central monitoring system 2000.

In some embodiments, central monitoring system 2000 receives data indicating the likelihood that a monitored individual is impaired from one or more different individual impairment processing engines including, but not limited to, voice based classification engine 197, movement based classification engine 198, visual based classification engine 199, alcohol impairment classification engine 168, and/or drug impairment classification engine 169. A multi-predictor classification engine 2050 applies a multi-predictor impairment model to a combination of two or more likelihoods of impairment received from respective impairment processing engines to yield a single likelihood of impairment as a classification output 2075.

The multi-predictor impairment model is trained by a multi-predictor classification training engine 2025. Multi-predictor classification training engine 2025 uses sample data 2030 to train the multi-predictor impairment model. Sample data 2030 includes two or more types of data each provided as respective predictors to multi-predictor classification training engine 2025. Such sample data 2030 may include a combination of, for example, two or more of movement data, facial image data, VOC sample data, or the like. Each of the aforementioned types of data may include a number of previously received indications of likelihood of impairment that have been previously classified by an expert based upon a user input 2002 with communication to the user providing the input being provided via a display 2035, that that were automatically classified by a classification engine from which the respective sample was provided (e.g., one of voice based classification engine 197, movement based classification engine 198, visual based classification engine 199, alcohol impairment classification engine 168, and/or drug impairment classification engine 169). Multi-predictor classification training engine 2025 may be any circuit and/or processor executing instructions that is capable of training a multi-predictor impairment model that receives two or more likelihood of impairment values, and adjusts the multi-predictor impairment model to improve the accuracy of a classification output generated based upon applying the multi-predictor impairment model to two or more inputs.

Figure 1E:
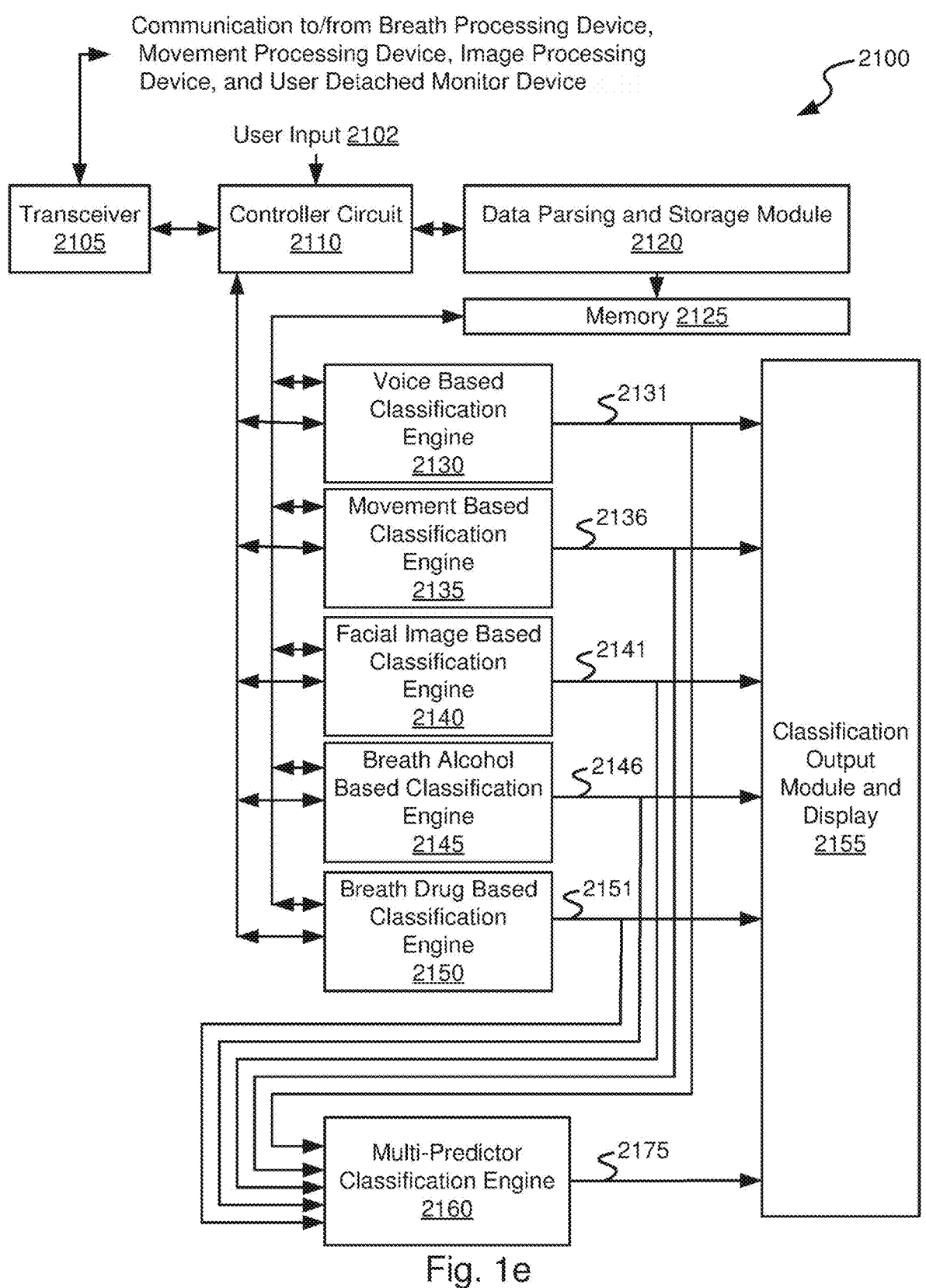
FIG. 1E is a block diagram of a central monitoring system capable of communicating with one or both of a user detached monitoring device and/or an impairment detection device and performing multi-predictor impairment classification and/or individual class impairment classification in accordance with other embodiments.

FIG. 1E is a block diagram is shown of a central monitoring system 2100 capable of communicating with one or both of user detached monitor device 120 and/or breath based impairment detection device 192, and performing multi-predictor impairment classification in accordance with various embodiments. As shown, central monitoring system 2100 includes a transceiver 2105 capable of receiving and sending communications to/from various processing devices including, but not limited to, user detached monitor device 120 and/or breath based impairment detection device 192.

The data transmitted via transceiver 2105 is provided from a controller circuit 2110, and the data received via transceiver 2105 is provided to controller circuit 2110. In some cases, controller circuit 2110 includes a processor. In various cases, controller circuit 2110 is part of an integrated circuit. In one or more cases, memory is included in an integrated circuit with controller circuit 2110. In various cases, the memory may include non-transient instructions (e.g., software or firmware-based based instructions) executable by controller circuit 2110 to perform and/or enable various functions associated with central monitoring system. In some embodiments, controller circuit 2110 executes instructions to perform one or more of the impairment determination processes discussed below. Controller circuit 2110 is communicably coupled to a memory 2125 where data may be stored and from which data may be retrieved.

A data parsing module 2120 extracts data received via transceiver 2105 to yield various classes of data (e.g., a voice data class, an image data class, an ambient temperature data class, a biometric data class, a VOC data class, a movement data class, a voice data class, and/or an alcohol data class). Each of the different data classes may be stored in different locations in memory 2125 of central monitoring system 2100.

In some embodiments, central monitoring system 2100 receives raw sensor data that may be used to determine a likelihood that a monitored individual is impaired. Such raw data may include, but is not limited to, voice data from a monitored individual that may be processed by a voice based classification engine 2130, movement data for a monitored individual that may be processed by a movement based classification engine 2135, facial image data for a monitored individual that may be processed by a facial image based classification engine 2140, breath alcohol data for a monitored individual that may be processed by a breath alcohol based classification engine 2145, and/or breath VOC data for a monitored individual that may be processed by a breath drug based classification engine 2150.

In some cases, voice based classification engine 2130 performs some processes similar to those discussed below in relation to FIG. 14; movement based classification engine 2135 performs some processes similar to those discussed below in relation to FIG. 15; facial image based classification engine 2140 performs some processes similar to those discussed below in relation to FIG. 16; breath alcohol based classification engine 2145 performs some processes similar to those discussed below in relation to FIG. 12; and breath drug based classification engine 2150 performs some processes similar to those discussed below in relation to FIGS. 17a-17b.

A resulting likelihood of impairment based upon voice data 2131, a resulting likelihood of impairment based upon movement data 2136, a resulting likelihood of impairment based upon facial image data 2141, a resulting likelihood of impairment based upon breath alcohol data 2146, and a resulting likelihood of impairment based upon breath drug data 2151 are provided to a classification output module and display 2155 and to a multi-predictor classification engine 2160. Classification output module and display 2155 is configured to display the various reported likelihoods.

Multi-predictor classification engine 2160 applies a multi-predictor impairment model to a combination of two or more likelihoods of impairment received from respective impairment processing engines to yield a single likelihood of impairment as a classification output 2175 that is also provided to classification output module and display 2155. As discussed above in relation to multi-predictor classification engine 2050 is trained by a multi-predictor classification training engine that uses sample data to train the multi-predictor impairment model.

Figure 2:
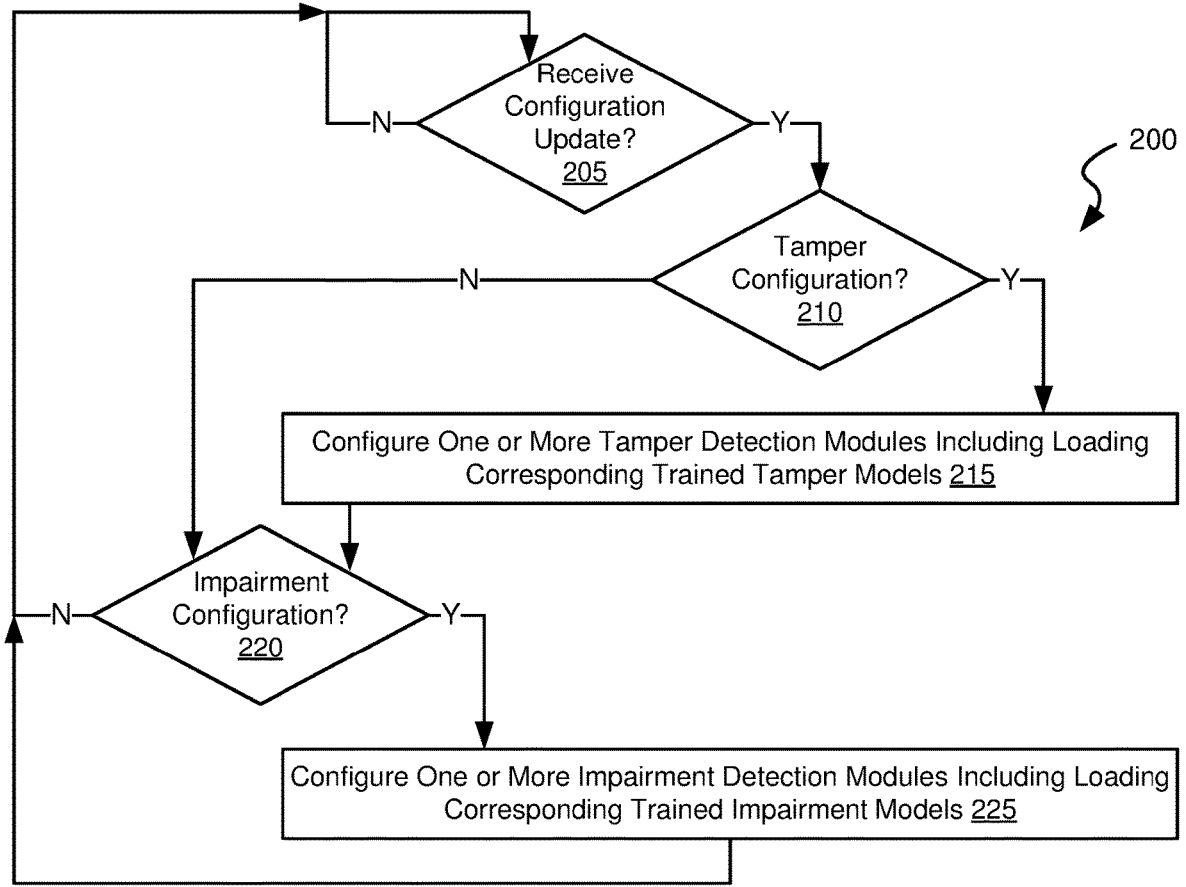
FIG. 2 is a flow diagram showing a method in accordance with some embodiments for configuring either a user detached monitor device or a breath based impairment detection device to perform impairment detection using one or more trained models.

FIG. 2 is a flow diagram showing a method in accordance with some embodiments for configuring either user detached monitor device 120 or breath based impairment detection device 192 to perform impairment detection using one or more trained models. Following flow diagram 200, it is determined if a configuration update has been received (block 205). A configuration update may be received, for example, from a central monitoring system. Such an update may be aa firmware update that changes the operational capability of the device receiving the configuration update. As just one example, a user may request that a breath based impairment detection device be changed to detect drug usage in additional to alcohol usage. In such a situation, an update to the firmware may be made that will result in detection of VOCs in the breath of a monitored individual in addition to detecting alcohol in the monitored individual's breath. Such configuration updates may include update machine learning models that are used in relation to respective impairment detection processes. Based upon the disclosure provided herein, one of ordinary skill in the art will recognize a variety of configuration updates that may be provided to one or both of user detached monitor device 120 or breath based impairment detection device 192 in accordance with different embodiments.

Where a configuration update is received (block 205), it is determined whether the received configuration update includes an update to a tamper configuration (block 210). Such a tamper configuration may be designed to assure that any impairment testing applied to a monitored individual is accurate. As just one example, a tamper configuration may be configured to determine whether a monitored individual is breathing properly into breath tube 190 of breath based impairment detection device 192. This process may be done, for example, similar to that discussed below in relation to FIG. 12. As another example, a tamper configuration may be configured to determine whether a monitored individual is standing too still during a movement based impairment detection process as more fully discussed below in relation to FIG. 15. Based upon the disclosure provided herein, one of ordinary skill in the art will recognize a variety of tamper configurations that may be received in relation to different embodiments.

Where a tamper configuration is received (block 210), any tamper detection modules associated with the receiving device are updated (block 215). Where, for example, the receiving device is breath based breath based impairment detection device 192 and the tamper is configuration is that of proper use of breath tube 190, the updated tamper configuration may include an updated machine learning model (i.e., an interference classification model) that has been trained with a group of previously classified images of both tamper evident uses of breath tube 190 and proper uses of breath tube 190. Based upon the disclosure provided herein, one of ordinary skill in the art will recognize a number of tamper configurations and corresponding tamper detection modules that may be updated in relation to different embodiments.

Where either no tamper configuration was received (block 210) or a received tamper configuration has been updated (block 215), it is determined if an impairment configuration has been received (block 220). Where, for example, the receiving device is breath based breath based impairment detection device 192 and the received impairment configuration is an update to a drug impairment test, the updated impairment configuration may include an updated machine learning model (i.e., a drug impairment model) that has been trained with a group of previously classified sets of breath data for both impaired and non-impaired individuals as more fully described below in relation to FIGS. 17a-17b. As another example where the receiving device is user detached monitor device 120 and the received impairment configuration is an update to a facial based impairment detection, the updated impairment configuration may include an updated machine learning model (i.e., a facial impairment model) that has been trained with a group of previously classified images of both impaired and non-impaired individuals as more fully described below in relation to FIG. 16. Based upon the disclosure provided herein, one of ordinary skill in the art will recognize a variety of impairment configurations that may be received in relation to different embodiments.

Where an impairment configuration is received (block 220), any impairment detection modules associated with the receiving device are updated (block 225). Where, for example, the receiving device is breath based breath based impairment detection device 192 and the received impairment configuration is an update to a drug impairment test, the updated impairment detection modules include breath sensor 166 and drug impairment classification engine 169.

As another example where the receiving device is user detached monitor device 120 and the received impairment configuration is an update to a facial based impairment detection, the updated impairment detection module may include visual based classification engine 199. Based upon the disclosure provided herein, one of ordinary skill in the art will recognize a variety of impairment configurations that may be received in relation to different embodiments.

Figure 3:
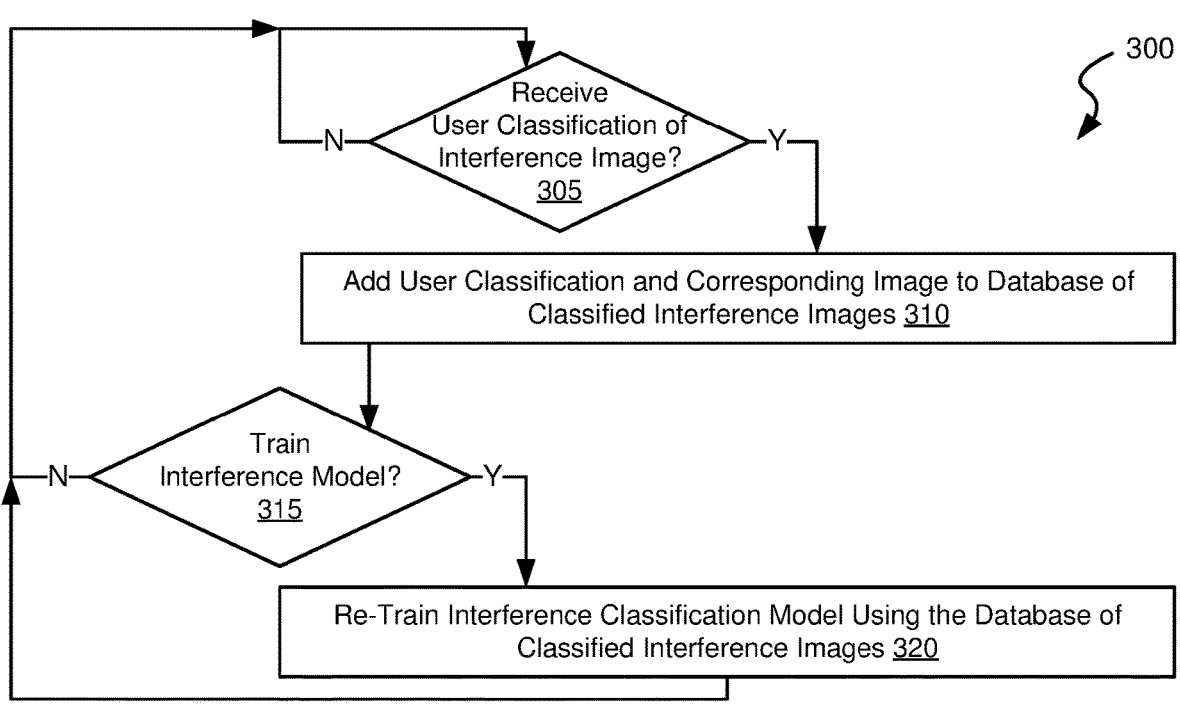
FIG. 3 is a flow diagram in accordance with some embodiments showing a method for training an interference classification model based at least in part upon newly received interference images.

Turning to FIG. 3, a flow diagram 300 shows a method for training an interference classification model based at least in part upon newly received interference images in accordance with some embodiments. Following flow diagram 300, it is determined whether a user classification of an image has been received (block 305). Images classified by a user as either indicating interference with breath tube 190 or no interference with breath tube 190 are valuable in training and re-training an interference classification model. User classification information may be received, for example, as user input 2002 of central monitoring system 2000 or user input 2102 of central monitoring system 2100. Based upon the disclosure provided herein, one of ordinary skill in the art will recognize a variety of mechanisms and processes that may be used to associated user classification input data with corresponding images.

A number of previously classified images showing a monitored individual while they are breathing into breath tube 190 may be included as sample data 2030 and used to train the interference classification model. As a starter, the images included may include those where interference is obvious, those where no interference is obvious, and those where interference or non-interference is less obvious. By using a broad array of sample images, an increase in the accuracy of the interference classification model can be achieved. As discussed below in relation to FIG. 12 user classification information may be requested in boundary conditions where the result of applying the interference classification model to an input image is ambiguous on whether the image shows interference or not. Such images showing boundary conditions that are classified by a user are valuable in increasing the accuracy of the interference classification model.

Where a user classification of an image has been received (block 305), the classification and corresponding image are added to a database of classified interference images (block 310). In some embodiments, this database is incorporated into memory 2125 or sample data 2030 that may be used in re-training the interference classification model that is used in relation to facial image based classification engine 2140 and/or visual based classification engine 199. The classification and corresponding image will indicate whether the image shows a person interfering with breath tube 190 or not interfering with breath tube 190. In some embodiments, classifications automatically indicated by the interference classification model are included along with classifications provided by a user as more fully discussed below in relation to FIG. 12. In other embodiments, only classifications provided by the user are updated to the database.

It is determined whether it is time to re-train the interference classification model (block 315). This re-training may be periodically performed based upon a passage of time or an increase in new samples. Where the re-training is done based upon the passage of time, determining that it is time to re-train the interference classification model (block 315) is based upon a timer. Where, on the other hand, the re-training is done based upon the availability of new samples, determining that it is time to re-train the interference classification model (block 315) is based upon a count of newly available samples since the last training. Where it is determined that it is time to re-train the interference classification model (block 315), the database of classified interference images is accessed and used to train the interference classification model (block 320). This re-training may be done using any model training process known in the art.

Figure 4:
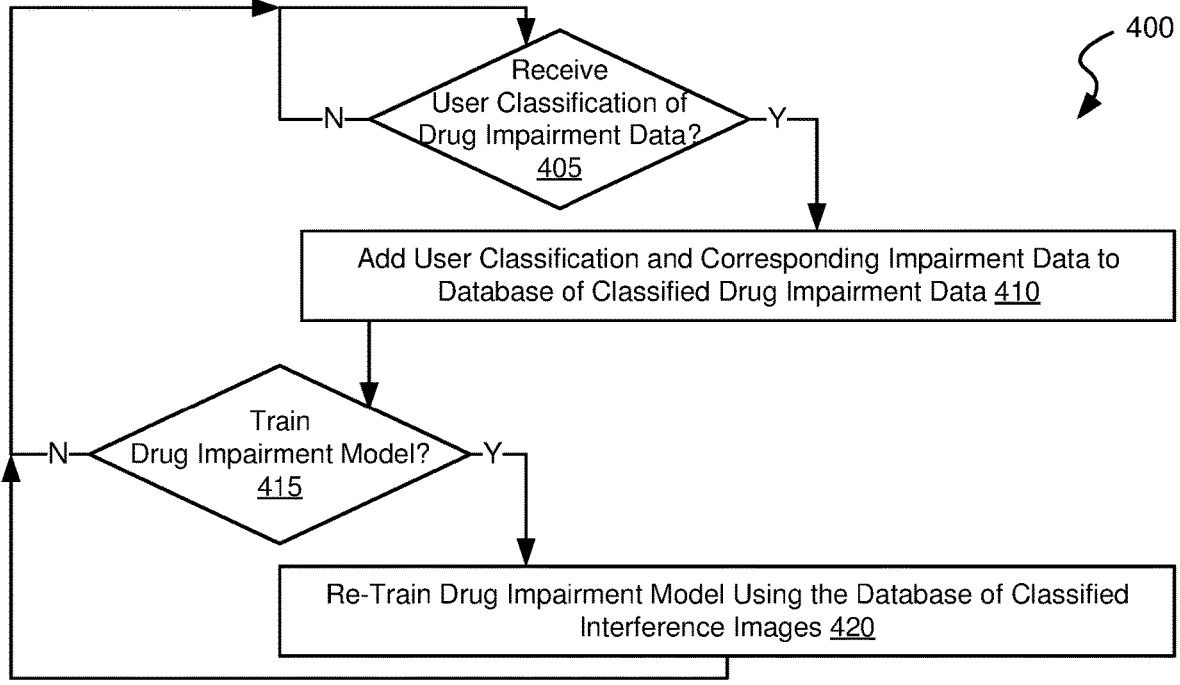
FIG. 4 is a flow diagram in accordance with some embodiments showing a method for training a drug impairment model based at least in part upon newly received drug impairment data.

Turning to FIG. 4, a flow diagram 400 shows a method in accordance with some embodiments for training a drug impairment model based at least in part upon newly received drug impairment data. Following flow diagram 400, it is determined whether a user classification of drug impairment data has been received (block 405). Drug impairment data classified by a user as either indicating impairment or non-impairment are valuable in training and re-training a drug impairment model. User classification information may be received, for example, as user input 2002 of central monitoring system 2000 or user input 2102 of central monitoring system 2100. Based upon the disclosure provided herein, one of ordinary skill in the art will recognize a variety of mechanisms and processes that may be used to associated user classification input data with corresponding drug impairment data.

A number of previously classified drug impairment data sets derived from the breath of a monitored individual while they are breathing into breath tube 190 may be included as sample data 2030 and used to train the drug impairment model. As a starter, the drug impairment data sets included may include those where impairment is obvious, those where no impairment is obvious, and those where impairment or non-impairment is less obvious. By using a broad array of sample drug impairment data sets, an increase in the accuracy of the drug impairment model can be achieved. As discussed below in relation to FIGS. 17a-17b user classification information may be requested in boundary conditions where the result of applying the drug impairment model to input drug impairment data is ambiguous on whether the data shows impairment or not. Such drug impairment data showing boundary conditions that are classified by a user are valuable in increasing the accuracy of the drug impairment model.

Where a user classification of drug impairment data has been received (block 405), the classification and corresponding drug impairment data are added to a database of classified drug impairment data sets (block 410). In some embodiments, this database is incorporated into memory 2125 or sample data 2030 that may be used in re-training the drug impairment model that is used in relation to breath drug classification engine 2145 and/or drug impairment classification engine 169. The classification and corresponding drug impairment data will indicate whether the data indicates drug impairment or not. In some embodiments, classifications automatically indicated by the drug impairment model are included along with classifications provided by a user as more fully discussed below in relation to FIGS. 17a-17b. In other embodiments, only classifications provided by the user are updated to the database.

It is determined whether it is time to re-train the drug impairment model (block 415). This re-training may be periodically performed based upon a passage of time or an increase in new samples. Where the re-training is done based upon the passage of time, determining that it is time to re-train the drug impairment model (block 415) is based upon a timer. Where, on the other hand, the re-training is done based upon the availability of new samples, determining that it is time to re-train the drug impairment model (block 415) is based upon a count of newly available samples since the last training. Where it is determined that it is time to re-train the drug impairment model (block 415), the database of classified drug impairment data sets is accessed and used to train the drug impairment model (block 420). This re-training may be done using any model training process known in the art.

Figure 5:
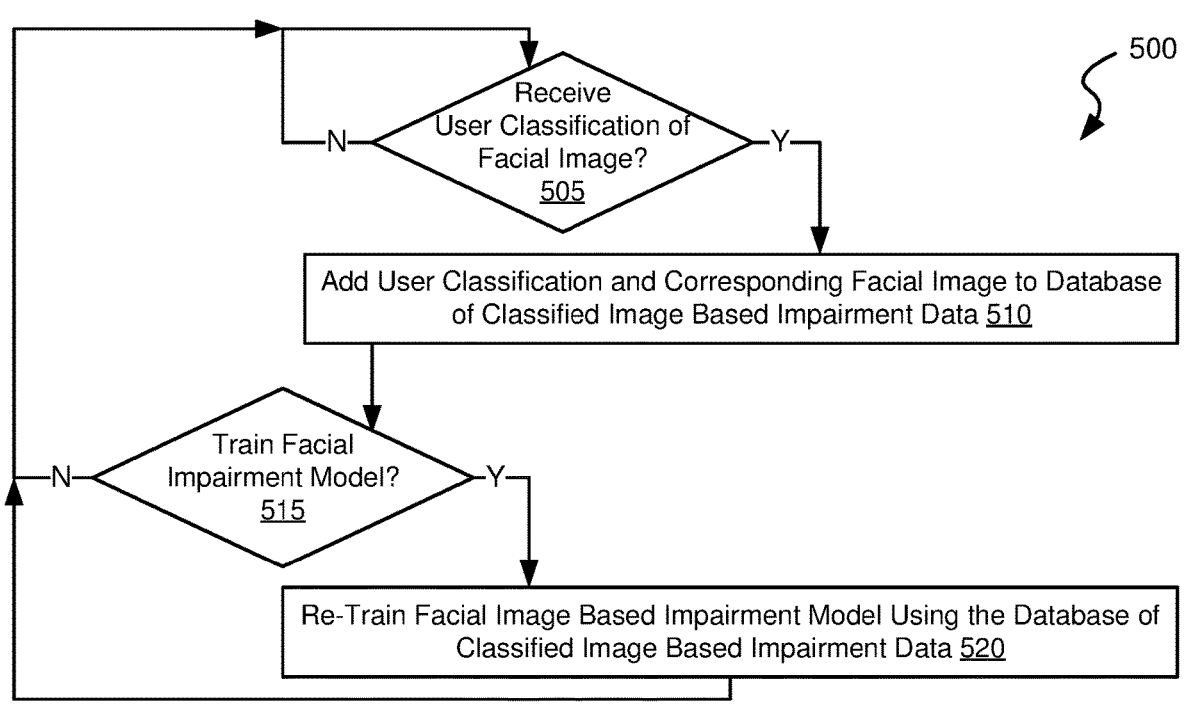
FIG. 5 is a flow diagram in accordance with some embodiments showing a method for training a facial image based impairment model based at least in part upon newly received facial image data.

Turning to FIG. 5, a flow diagram 500 shows a method in accordance with some embodiments for training a facial image based impairment model based at least in part upon newly received facial image data. Following flow diagram 500, it is determined whether a user classification of facial image has been received (block 505). Facial images classified by a user as either indicating impairment or non-impairment are valuable in training and re-training a facial image based impairment model. User classification information may be received, for example, as user input 2002 of central monitoring system 2000 or user input 2102 of central monitoring system 2100. Based upon the disclosure provided herein, one of ordinary skill in the art will recognize a variety of mechanisms and processes that may be used to associated user classification input data with corresponding drug impairment data.

A number of previously classified facial images captured of a monitored individual may be included as sample data 2030 and used to train the facial image based impairment model. As a starter, the facial images may include those where impairment is obvious, those where no impairment is obvious, and those where impairment or non-impairment is less obvious. By using a broad array of facial imaged, an increase in the accuracy of the facial image based impairment model can be achieved. As discussed below in relation to FIG. 16 user classification information may be requested in boundary conditions where the result of applying the facial image based impairment model to received facial images is ambiguous on whether the data shows impairment or not. Such facial images showing boundary conditions that are classified by a user are valuable in increasing the accuracy of the facial image based impairment model.

Where a user classification of a facial image has been received (block 505), the classification and corresponding facial image are added to a database of classified facial impairment images (block 510). In some embodiments, this database is incorporated into memory 2125 or sample data 2030 that may be used in re-training the facial image based impairment model that is used in relation to facial image classification engine 2140 and/or visual based classification engine 199. The classification and corresponding facial image will indicate whether the data indicates impairment or not. In some embodiments, classifications automatically indicated by the facial image based impairment model are included along with classifications provided by a user as more fully discussed below in relation to FIG. 16. In other embodiments, only classifications provided by the user are updated to the database.

It is determined whether it is time to re-train the facial image based impairment model (block 515). This re-training may be periodically performed based upon a passage of time or an increase in new samples. Where the re-training is done based upon the passage of time, determining that it is time to re-train the facial image based impairment model (block 515) is based upon a timer. Where, on the other hand, the re-training is done based upon the availability of new samples, determining that it is time to re-train the facial image based impairment model (block 515) is based upon a count of newly available samples since the last training. Where it is determined that it is time to re-train the facial image based impairment model (block 515), the database of classified facial images is accessed and used to train the facial image based impairment model (block 520). This re-training may be done using any model training process known in the art.

Figure 6:
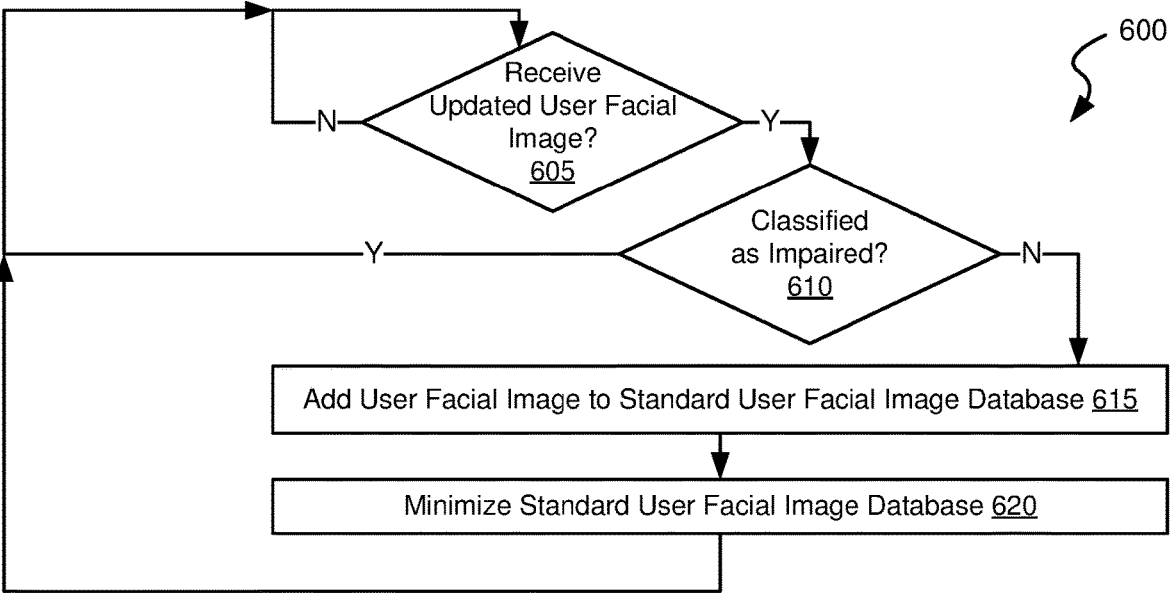
FIG. 6 is a flow diagram in accordance with various embodiments showing a method for maintaining a standard user facial image database updated with newly received facial images classified as non-impaired.

Turning to FIG. 6, a flow diagram 600 shows a method in accordance with various embodiments for maintaining a standard user facial image database updated with newly received facial images classified as non-impaired. Following flow diagram 600, it is determined whether a new facial image has been received (block 605). Where a new facial image has been received (block 605), it is determined whether the facial image has been classified as impaired (block 610). Where the newly received facial image has been classified as non-impaired (block 610), the newly received facial image is added to a database of facial images exclusive to the particular monitored individual from whom the newly received facial image was captured (block 615). Such images of the monitored individual in an unimpaired state are referred to as standard user facial images and are used to make a threshold impairment decision as more fully described below in relation to FIG. 16. This database of standard user facial images may be deployed in any or a combination of memory 2125, sample data 2030, and/or memory 124. This database of standard user facial images is minimized to reduce the amount of memory required to hold all of the collected facial images (block 620). Such minimization may include removing the oldest facial images from the database to assure that the database has the most recent images of the monitored individual, and/or to remove facial images that were only marginally classified as non-impaired (i.e., facial images that garnered relatively high scores from the facial image based impairment model compared to other facial images in the database, but were nonetheless classified as non-impaired). Based upon the disclosure provided herein, one of ordinary skill in the art will recognize a variety of minimizing processes that may be used in relation to different embodiments.

Figure 7:
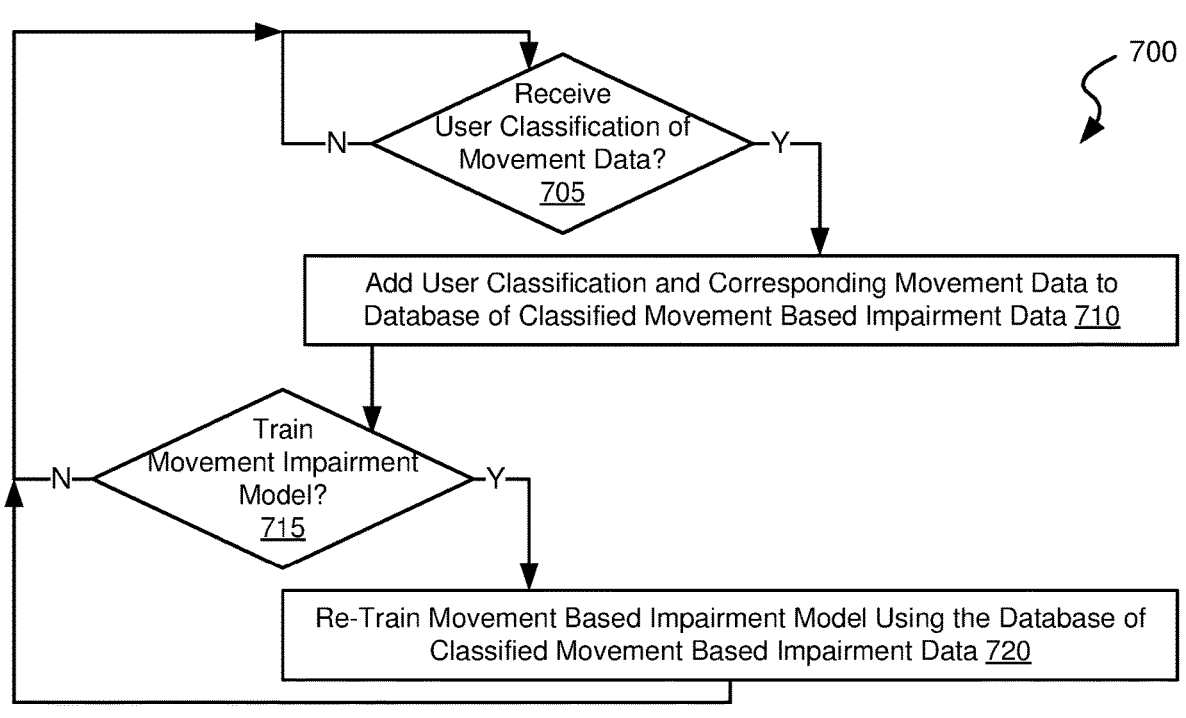
FIG. 7 is a flow diagram in accordance with some embodiments showing a method for training a movement based impairment model based at least in part upon newly received movement data.

Turning to FIG. 7, a flow diagram 700 shows a method in accordance with various embodiments for training a movement based impairment model based at least in part upon newly received movement data. Following flow diagram 700, it is determined whether a user classification of movement data has been received (block 705). Movement data classified by a user as either indicating impairment or non-impairment are valuable in training and re-training a movement based impairment model. User classification information may be received, for example, as user input 2002 of central monitoring system 2000 or user input 2102 of central monitoring system 2100. Based upon the disclosure provided herein, one of ordinary skill in the art will recognize a variety of mechanisms and processes that may be used to associated user classification input data with corresponding movement data.

A number of previously movement data sets captured about a monitored individual may be included as sample data 2030 and used to train the movement based impairment model. As a starter, the movement data may include that where impairment is obvious, that where no impairment is obvious, and that where impairment or non-impairment is less obvious. By using a broad array of movement data, an increase in the accuracy of the movement based impairment model can be achieved. As discussed below in relation to FIG. 15 user classification information may be requested in boundary conditions where the result of applying the movement based impairment model to received facial images is ambiguous on whether the data shows impairment or not. Such movement data showing boundary conditions that are classified by a user are valuable in increasing the accuracy of the movement based impairment model.

Where a user classification of movement data has been received (block 705), the classification and corresponding movement data are added to a database of classified movement data sets (block 710). In some embodiments, this database is incorporated into memory 2125 or sample data 2030 that may be used in re-training the facial image based impairment model that is used in relation to movement based classification engine 2135 and/or movement based classification engine 198. The classification and corresponding movement data will indicate whether the data indicates impairment or not. In some embodiments, classifications automatically indicated by the movement based impairment model are included along with classifications provided by a user as more fully discussed below in relation to FIG. 15. In other embodiments, only classifications provided by the user are updated to the database.

It is determined whether it is time to re-train the movement based impairment model (block 715). This re-training may be periodically performed based upon a passage of time or an increase in new samples. Where the re-training is done based upon the passage of time, determining that it is time to re-train the movement based impairment model (block 715) is based upon a timer. Where, on the other hand, the re-training is done based upon the availability of new samples, determining that it is time to re-train the movement based impairment model (block 715) is based upon a count of newly available samples since the last training. Where it is determined that it is time to re-train the movement based impairment model (block 715), the database of classified movement data sets is accessed and used to train the movement based impairment model (block 720). This re-training may be done using any model training process known in the art.

Figure 8:
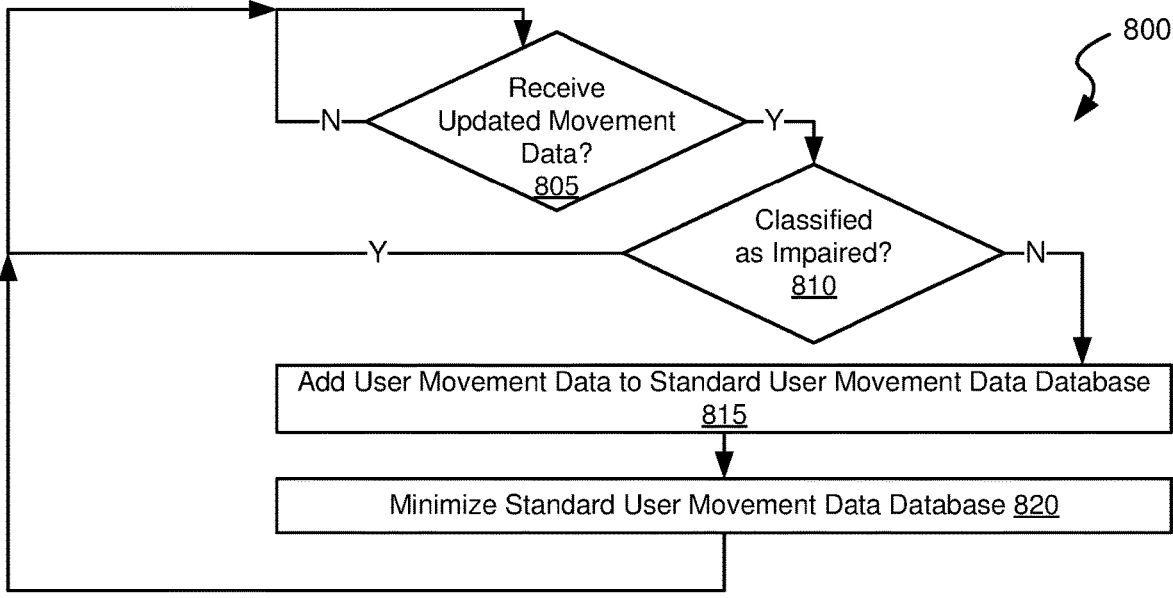
FIG. 8 is a flow diagram in accordance with various embodiments showing a method for maintaining a standard user movement database updated with newly received movement data classified as non-impaired.

Turning to FIG. 8, a flow diagram 800 shows a method in accordance with some embodiments for maintaining a standard user movement database updated with newly received movement data classified as non-impaired. Following flow diagram 800, it is determined whether a new movement data has been received (block 805). Where a new movement data has been received (block 805), it is determined whether the movement data has been classified as impaired (block 810). Where the newly received movement data been classified as non-impaired (block 810), the newly received movement data is added to a database of movement data sets exclusive to the particular monitored individual about whom the newly received movement data was captured (block 815). Such movement data of the monitored individual in an unimpaired state are referred to as standard movement data and are used to make a threshold impairment decision as more fully described below in relation to FIG. 15. This database of standard user movement data sets may be deployed in any or a combination of memory 2125, sample data 2030, and/or memory 124. This database of standard movement data sets is minimized to reduce the amount of memory required to hold all of the collected movement data sets (block 820). Such minimization may include removing the oldest movement data sets from the database to assure that the database has the most recent movement data for the monitored individual, and/or to remove movement data sets that were only marginally classified as non-impaired (i.e., movement data sets that garnered relatively high scores from the movement based impairment model compared to other movement data sets in the database, but were nonetheless classified as non-impaired). Based upon the disclosure provided herein, one of ordinary skill in the art will recognize a variety of minimizing processes that may be used in relation to different embodiments.

Figure 9:
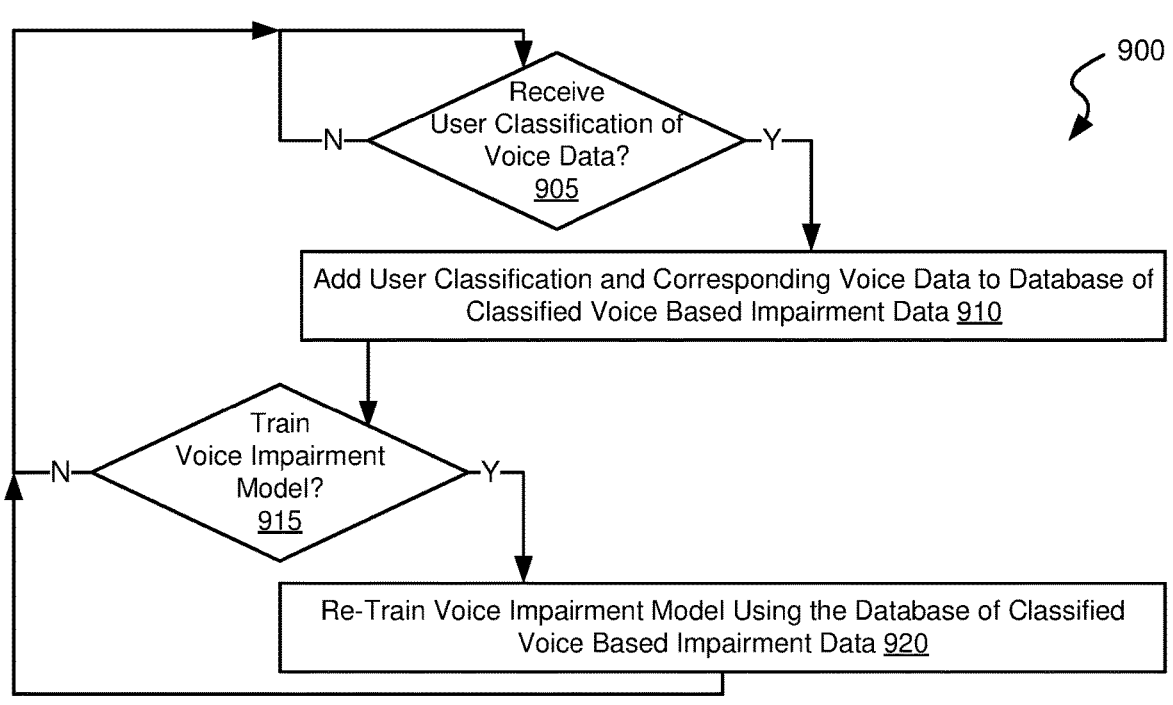
FIG. 9 is a flow diagram in accordance with some embodiments showing a method for training a voice data based impairment model based at least in part upon newly received voice data.

Turning to FIG. 9, a flow diagram 900 shows a method in accordance with various embodiments for training a voice data based impairment model based at least in part upon newly received voice data. Following flow diagram 900, it is determined whether a user classification of voice data has been received (block 905). Voice data classified by a user as either indicating impairment or non-impairment are valuable in training and re-training a voice based impairment model. User classification information may be received, for example, as user input 2002 of central monitoring system 2000 or user input 2102 of central monitoring system 2100. Based upon the disclosure provided herein, one of ordinary skill in the art will recognize a variety of mechanisms and processes that may be used to associated user classification input data with corresponding voice data.

A number of previously voice data sets captured about a monitored individual may be included as sample data 2030 and used to train the voice based impairment model. As a starter, the voice data may include that where impairment is obvious, that where no impairment is obvious, and that where impairment or non-impairment is less obvious. By using a broad array of voice data, an increase in the accuracy of the voice based impairment model can be achieved. As discussed below in relation to FIG. 14 user classification information may be requested in boundary conditions where the result of applying the voice based impairment model to received facial images is ambiguous on whether the data shows impairment or not. Such voice data showing boundary conditions that are classified by a user are valuable in increasing the accuracy of the voice based impairment model.

Where a user classification of voice data has been received (block 905), the classification and corresponding voice data are added to a database of classified voice data sets (block 910). In some embodiments, this database is incorporated into memory 2125 or sample data 2030 that may be used in re-training the facial image based impairment model that is used in relation to voice based classification engine 2130 and/or voice based classification engine 197. The classification and corresponding voice data will indicate whether the data indicates impairment or not. In some embodiments, classifications automatically indicated by the voice based impairment model are included along with classifications provided by a user as more fully discussed below in relation to FIG. 15. In other embodiments, only classifications provided by the user are updated to the database.

It is determined whether it is time to re-train the voice based impairment model (block 915). This re-training may be periodically performed based upon a passage of time or an increase in new samples. Where the re-training is done based upon the passage of time, determining that it is time to re-train the voice based impairment model (block 915) is based upon a timer. Where, on the other hand, the re-training is done based upon the availability of new samples, determining that it is time to re-train the voice based impairment model (block 915) is based upon a count of newly available samples since the last training. Where it is determined that it is time to re-train the voice based impairment model (block 915), the database of classified voice data sets is accessed and used to train the voice based impairment model (block 920). This re-training may be done using any model training process known in the art.

Figure 10:
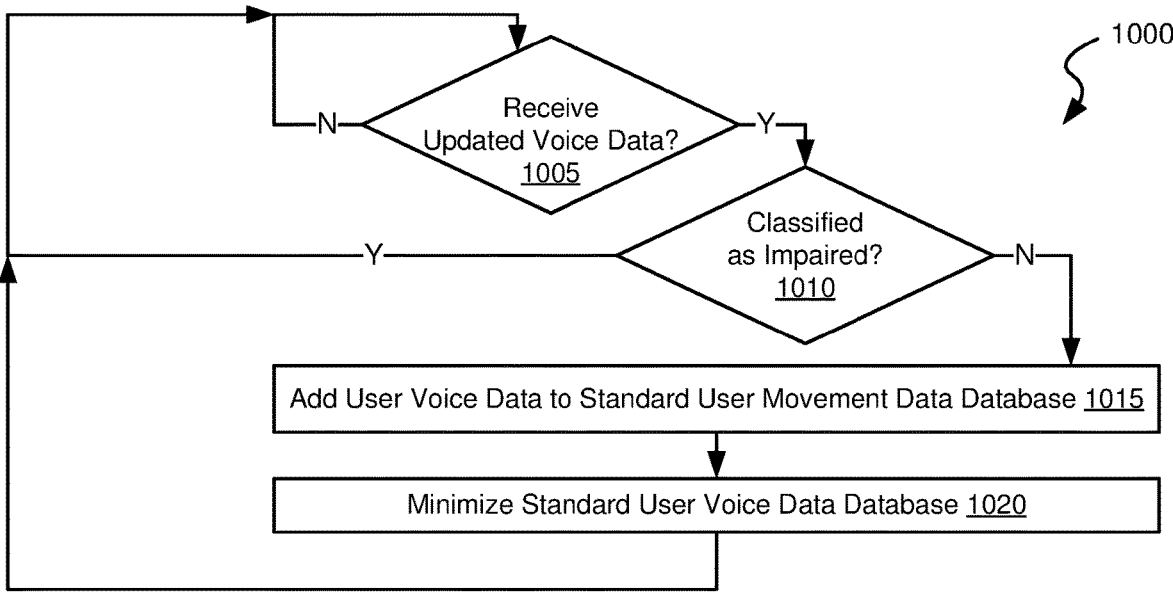
FIG. 10 is a flow diagram in accordance with various embodiments showing a method for maintaining a standard user voice database updated with newly received voice data classified as non-impaired.

Turning to FIG. 10, a flow diagram 1000 shows a method in accordance with some embodiments for maintaining a standard user voice database updated with newly received voice data classified as non-impaired. Following flow diagram 1000, it is determined whether a new voice data has been received (block 1005). Where a new voice data has been received (block 1005), it is determined whether the voice data has been classified as impaired (block 1010). Where the newly received voice data been classified as non-impaired (block 1010), the newly received voice data is added to a database of voice data sets exclusive to the particular monitored individual about whom the newly received voice data was captured (block 1015). Such voice data of the monitored individual in an unimpaired state are referred to as standard voice data and are used to make a threshold impairment decision as more fully described below in relation to FIG. 14. This database of standard user voice data sets may be deployed in any or a combination of memory 2125, sample data 2030, and/or memory 124. This database of standard voice data sets is minimized to reduce the amount of memory required to hold all of the collected voice data sets (block 1020). Such minimization may include removing the oldest voice data sets from the database to assure that the database has the most recent voice data for the monitored individual, and/or to remove voice data sets that were only marginally classified as non-impaired (i.e., voice data sets that garnered relatively high scores from the voice based impairment model compared to other voice data sets in the database, but were nonetheless classified as non-impaired). Based upon the disclosure provided herein, one of ordinary skill in the art will recognize a variety of minimizing processes that may be used in relation to different embodiments.

Figure 11:
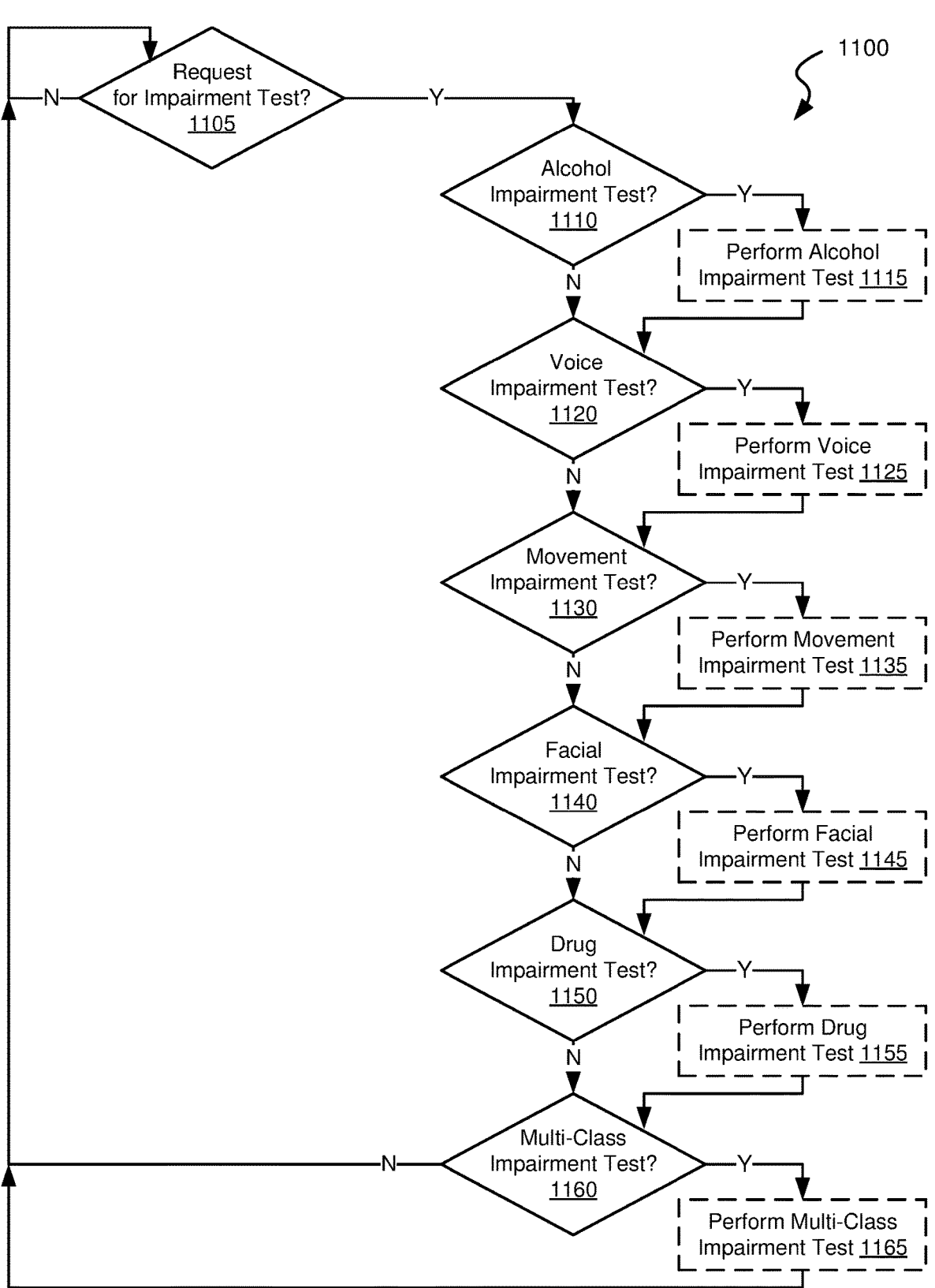
FIG. 11 is a flow diagram showing a method in accordance with some embodiments for determining impairment using selectively applied impairment models and processes.

Turning to FIG. 11, a flow diagram 1100 shows a method in accordance with some embodiments for determining impairment using selectively applied impairment models and processes. Following flow diagram 1100, it is determined whether a request for an impairment test has been received (block 1105). Such a request may be received, for example, from a supervising official charged with determining an impairment status of a monitored individual. As another example, such a request may be pre-programmed to occur in accordance with a schedule. Based upon the disclosure provided herein, one of ordinary skill in the art will recognize a variety of mechanisms and/or processes that may be used in receiving an impairment test request, and/or a number of individuals and/or pre-programmed schedules that may be responsible for making such requests. The received request for an impairment test may request one or more impairment tests.

Of note, not all systems will provide an ability to perform all tests. For example, an impairment testing system including only breath based impairment device 192 standing alone. In such a system, it could be that only drug based impairment testing and/or alcohol based impairment testing are offered. As another example, an impairment testing system including only user detached monitor device 120 standing alone. In such a system, it could be that only voice based impairment testing, movement based impairment testing, and/or facial image based impairment testing. In a system including both breath based impairment device 192 and user detached monitor device 120, any or all of voice based impairment testing, movement based impairment testing, facial image based impairment testing, drug based impairment testing, and/or alcohol based impairment testing are offered. As yet another example of a system including a central processing system, breath based impairment device 192, and user detached monitor device 120, any or all of voice based impairment testing, movement based impairment testing, facial image based impairment testing, drug based impairment testing, alcohol based impairment, and/or multi-predictor impairment testing are offered. Based upon the disclosure provided herein, one of ordinary skill in the art will recognize a variety of equipment combinations and/or impairment testing capabilities that can be offered in relation to different embodiments.

Where a request for an impairment test is received (block 1105), it is determined if the received request includes a request to perform an alcohol impairment test (block 1110). Where an alcohol impairment test is requested (block 1110), an alcohol impairment test is performed (block 1115). This is shown in a dashed line because the process is described in more detail below in relation to FIG. 12 below.

Once either the alcohol impairment test has been performed (block 1115) or no alcohol impairment test was requested (block 1110), it is determined if the received request includes a request to perform a voice impairment test (block 1120). Where a voice impairment test is requested (block 1120), a voice impairment test is performed (block 1125). This is shown in a dashed line because the process is described in more detail below in relation to FIG. 14 below.

Once either the voice impairment test has been performed (block 1125) or no voice impairment test was requested (block 1120), it is determined if the received request includes a request to perform a movement impairment test (block 1130). Where a movement impairment test is requested (block 1130), a movement impairment test is performed (block 1135). This is shown in a dashed line because the process is described in more detail below in relation to FIG. 15 below.

Once either the movement impairment test has been performed (block 1135) or no movement impairment test was requested (block 1130), it is determined if the received request includes a request to perform a facial impairment test (block 1140). Where a facial impairment test is requested (block 1140), a facial impairment test is performed (block 1145). This is shown in a dashed line because the process is described in more detail below in relation to FIG. 16 below.

Once either the facial impairment test has been performed (block 1145) or no facial impairment test was requested (block 1140), it is determined if the received request includes a request to perform a drug impairment test (block 1150). Where a drug impairment test is requested (block 1150), a drug impairment test is performed (block 1155). This is shown in a dashed line because the process is described in more detail below in relation to FIGS. 17*a*-17*b* below.

Once either the drug impairment test has been performed (block 1155) or no drug impairment test was requested (block 1150), it is determined if the received request includes a request to perform a multi-predictor impairment test (block 1160). Where a multi-predictor impairment test is requested (block 1160), a multi-predictor impairment test is performed (block 1165). This is shown in a dashed line because the process is described in more detail below in relation to FIG. 18 below.

Figure 12:
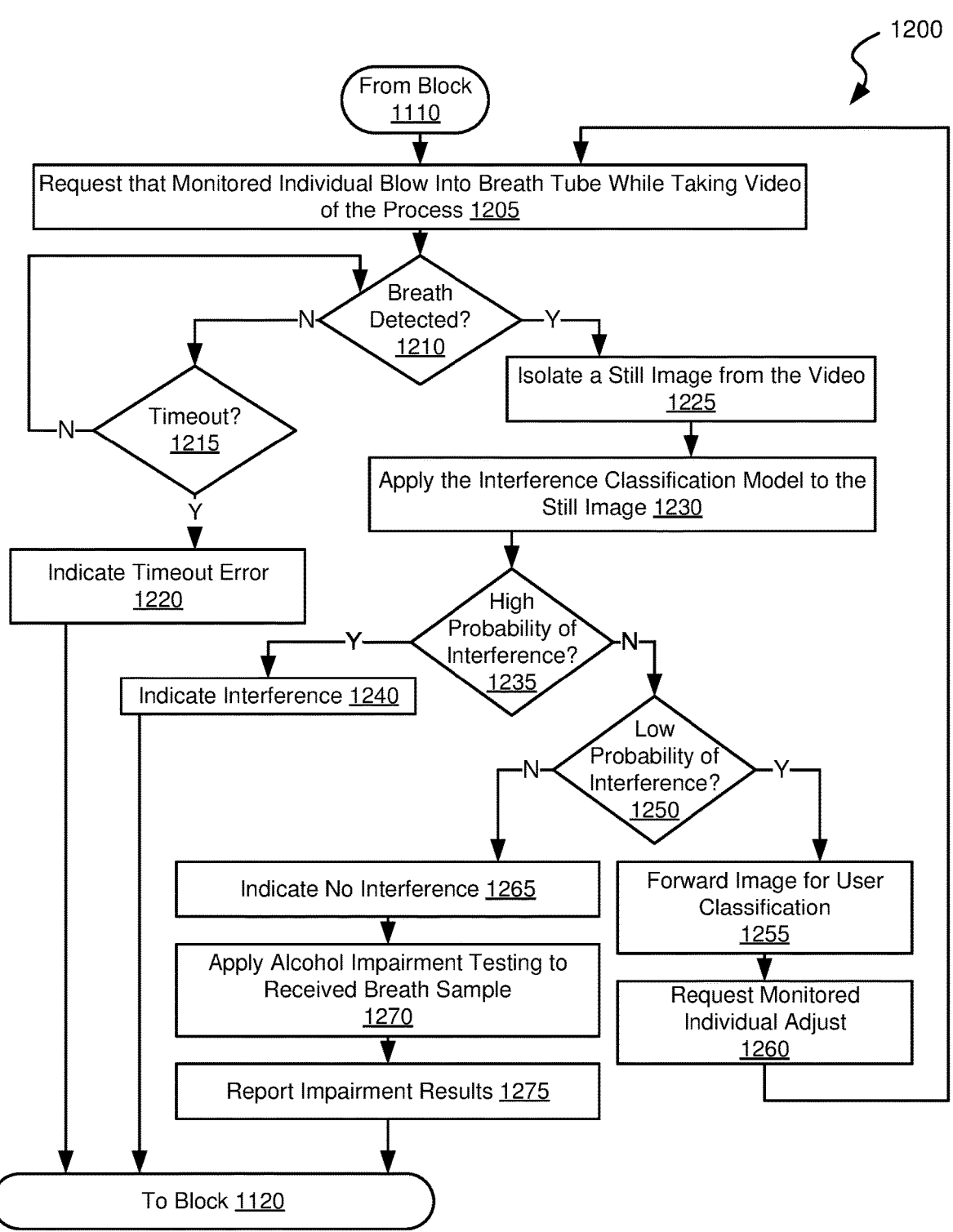
FIG. 12 is a flow diagram showing a method in accordance with various embodiments for determining impairment based upon breath alcohol measurements.

Turning to FIG. 12, a flow diagram 1200 shows a method in accordance with various embodiments for determining impairment based upon breath alcohol measurements. Flow diagram 1200 represents block 1115 and thus begins from block 1110 of the previously described FIG. 11. The processes of flow diagram 1200 may be executed on one of user detached monitor device 120 or breath based impairment detection device 192 depending upon the system implementation, and/or a combination of one of user detached monitor device 120 or breath based impairment detection device 192 and one of central monitoring system 2000 or central monitoring system 2100. Following flow diagram 1200, a request is made for the monitored individual to blow into breath tube 190 while taking a video using one of forward camera 172 or reverse camera 173 of user detached monitor device including the monitored individual's face and surrounding region while blowing (block 1205). This request may be provided via a display on either or both of user detached monitor device 120 and/or breath based impairment detection device 192.

A sensor on breath based impairment detection device 192 detects whether at least a minimum gas flow is reported from breath tube 190 (block 1210). This sensing may be done using any sensor known in the art for detecting gas flow volume. The sensor may be included as part of breath sensor 166 in breath based impairment detection device 192, with the information from the sensor being provided to one or both of alcohol impairment classification engine 168 and/or drug impairment classification engine 169. Where it is determined that insufficient gas flow has been detected by the sensor (block 1210), it is determined whether a timeout condition has been met (block 1215). A monitored individual is given a defined time period to comply with the request, and after the defined time period has passed the timeout condition is met. If the timeout condition has been met (block 1220), a timeout error is indicated (block 1220) and the processing returns to block 1120 of FIG. 11 without rendering an analysis of whether the monitored individual is impaired by alcohol.

Figure 13A:
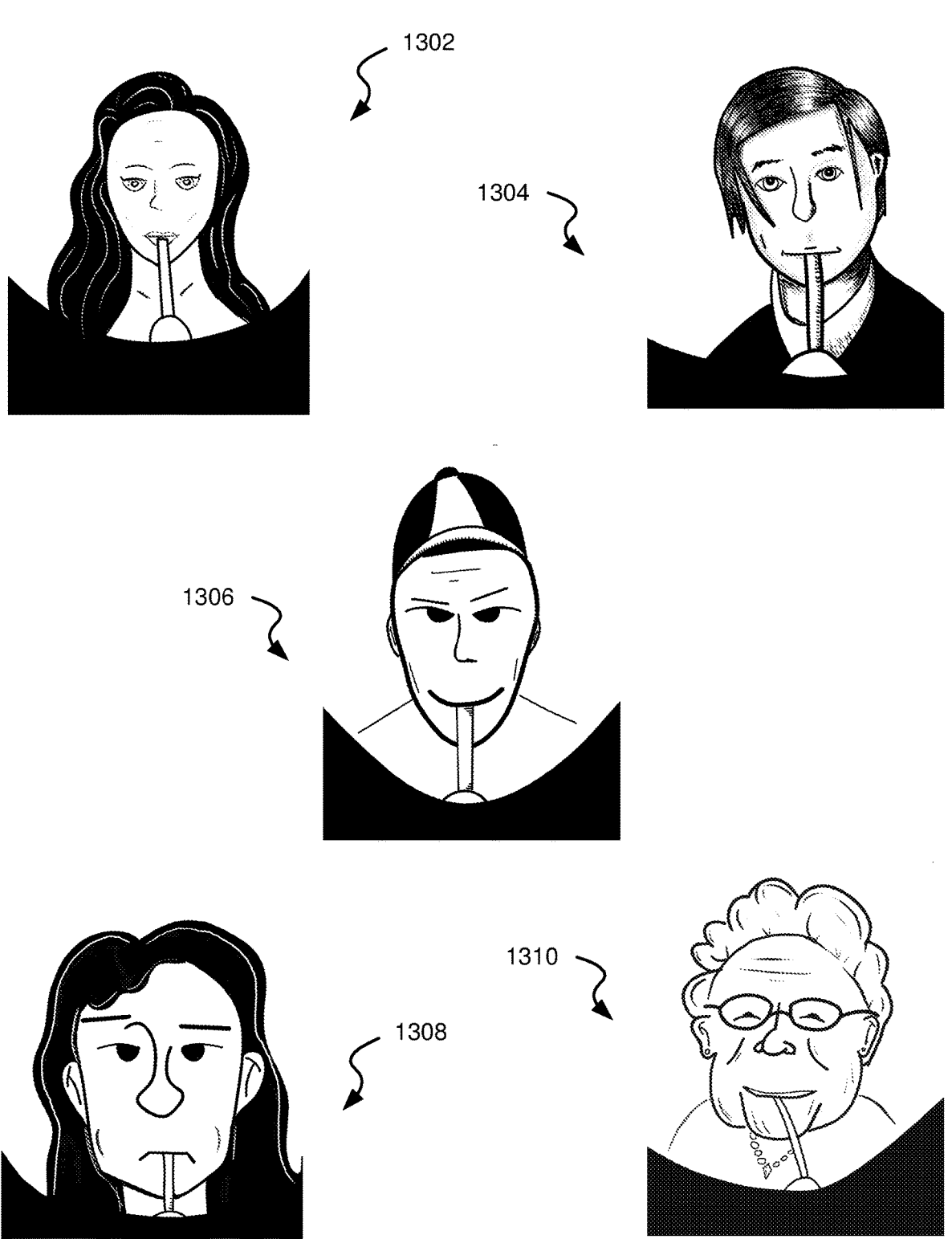
FIGS. 13*a*-13*b* show example images used in relation to some embodiments for determining interference with obtaining breath samples that may be used in relation to different embodiments.
Figure 13B:
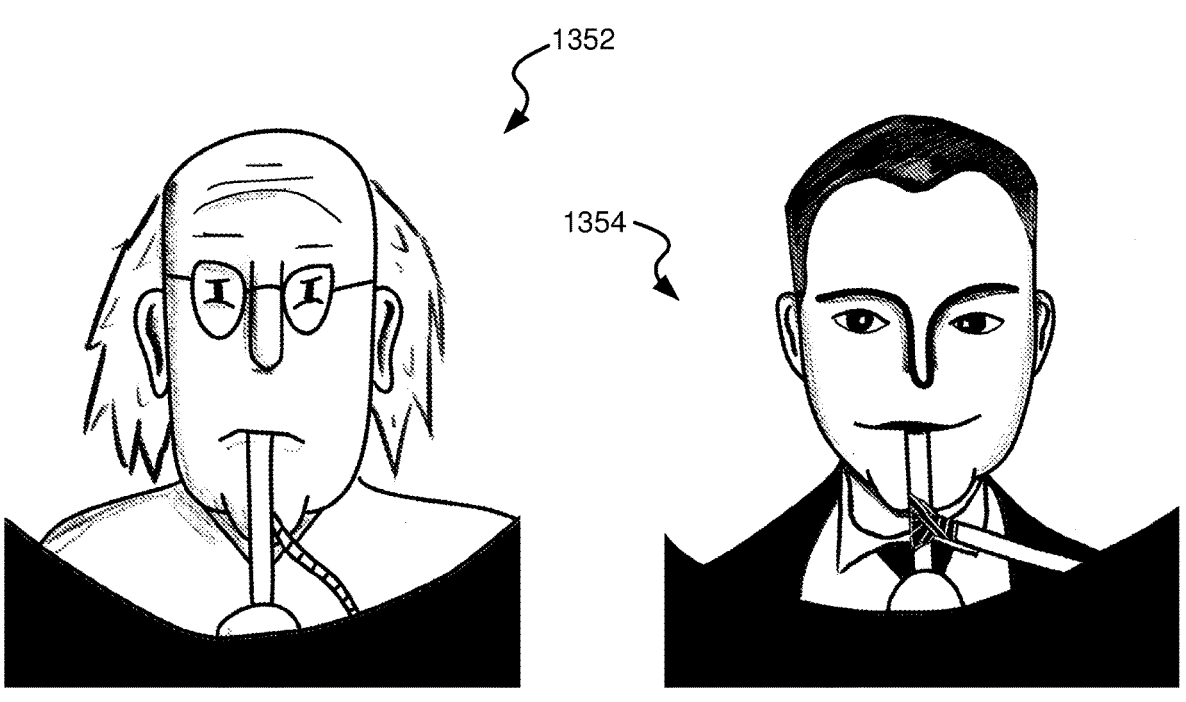
Figure 13B:
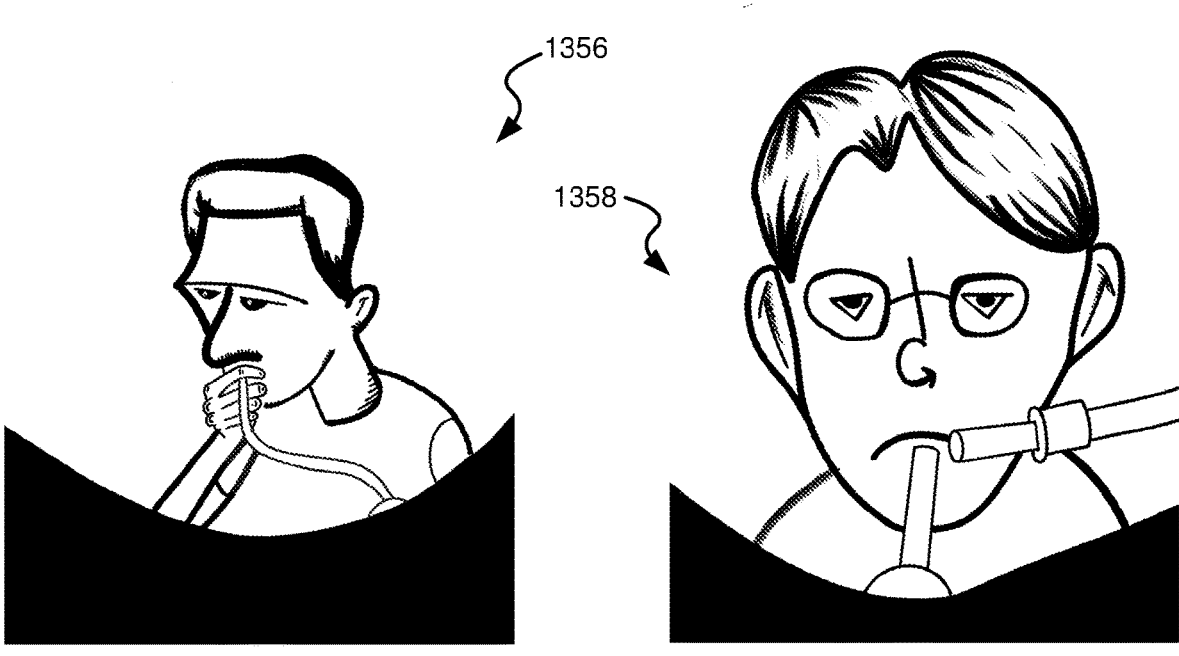

Alternatively, where it is determined that sufficient gas flow has been detected by the sensor (block 1210), a still image from the video of the monitored individual's face and surrounding area is isolated (block 1225). An interference classification model is applied to the still image to yield an indication of whether the monitored individual is interfering with breath tube (block 1230). As discussed above in relation to FIG. 3, the interference classification model is trained using a number of previously classified images showing a monitored individual while they are breathing into breath tube 190. The images may be derived from a large number of different monitored individuals, and have been classified as either indicating interference with breath tube 190 or no interference with breath tube 190. In some cases the classification is based upon a user input 2002 of central monitoring system 2000 or user input 2102 of central monitoring system 2100. In other cases, the classification is based upon the output from the user classification model. FIG. 13a are drawings representing a number of example still images 1302, 1304, 1306, 1308, 1310 each showing an respective individual with a breath tube properly inserted in their mouth while breathing, and without any addition elements included in the image that appear to be interfering with the test. FIG. 13b are drawings representing a number of example still images 1352, 1354, 1356, 1358 each showing an respective individual interfering with a breath tube. Still image 1352 shows an individual with both the breath tube and a secondary tube inserted into their mouth. In such an approach, a gas can be blown into the individual's mouth that flows out through the breath tube simulating breath. Still image 1354 shows an individual with the breath tube inserted in their mouth, and a secondary tube connected to into the breath tube. In such an approach, a gas can be blown from the secondary tube into the breath tube simulating breath. Still image 1356 shows an individual with the breath tube inserted in their mouth, but their hand is over their mouth and their head is turned potentially hiding a secondary tube. Still image 1356 shows an individual with the breath tube near their mouth along with a secondary tube. In such an approach, a gas can be blown toward the individual's mouth from the secondary tube and into the breath tube simulating breath.

In some embodiments, the interference classification model is a TensorFlow™ backbone used to generate a model that can be exported to a selected platform. Based upon the disclosure provided herein, one of ordinary skill in the art will recognize a variety of machine learning model types that may be trained using images of individuals blowing in a breath tube to determine whether a newly received image shows an individual properly using the breath tube.

The output from the interference classification model indicates a likelihood that the monitored individual is interfering with breath tube 190 or not using it properly. It is determined whether the likelihood value received from the interference classification model is higher than a high probability value (block 1235). Such a high probability value is selected as high enough to warrant indicating interference without having a human user consider the image. In some embodiments the high probability value is user programmable. Where the likelihood value received from the interference classification model is higher than the high probability value (block 1235), an interference is indicated (block 1240) and the processing returns to block 1120 of FIG. 11 without rendering an analysis of whether the monitored individual is impaired by alcohol.

Where, on the other hand, the likelihood value received from the interference classification model is not higher than the high probability value (block 1235), it is determined whether the likelihood value received from the interference classification model is lower than a low probability value (block 1250). Such a low probability value is selected as low enough to warrant indicating no interference without having a human user consider the image. In some embodiments the low probability value is user programmable. Where the likelihood value received from the interference classification model is lower than the low probability value (block 1250), no interference is indicated (block 1265). In this situation, alcohol impairment testing applied to the received breath sample is recorded as impairment results (block 1270), and the impairment results are reported (block 1275). In some embodiments, the alcohol impairment testing is a standard breath based alcohol detection as is known in the art. Having reported the impairment results, the process then returns to block 1120 of FIG. 11.

Alternatively, where the likelihood value received from the interference classification model is not lower than the low probability value (block 1250), an ambiguous condition has occurred. In such a situation, the still image of the monitored individual is forwarded to a user for classification (block 1255). The user may be, for example, a human responsible for making final determinations of interference based upon the still image. In some cases, the human may be a supervising authority of the monitored individual. This process may forward the image to a central monitoring system (e.g., central monitoring system 2100) which is capable of accepting user input (e.g., user input 2102). The user classification (i.e., classified as interference or no interference) is stored to a database where it may be used in a future re-training of the interference classification model as discussed above in relation to FIG. 3.

In addition, a request is made to the monitored individual to adjust how they are using the breath tube (block 1260). This request may be made, for example, by an audio message played on user detached monitor device 120. Based upon the disclosure provided herein, one of ordinary skill in the art will recognize a variety of mechanisms and/or processes that may be used to deliver a request to the monitored individual in accordance with different embodiments. The process then returns to block 1205 where the process begins again.

Figure 14:
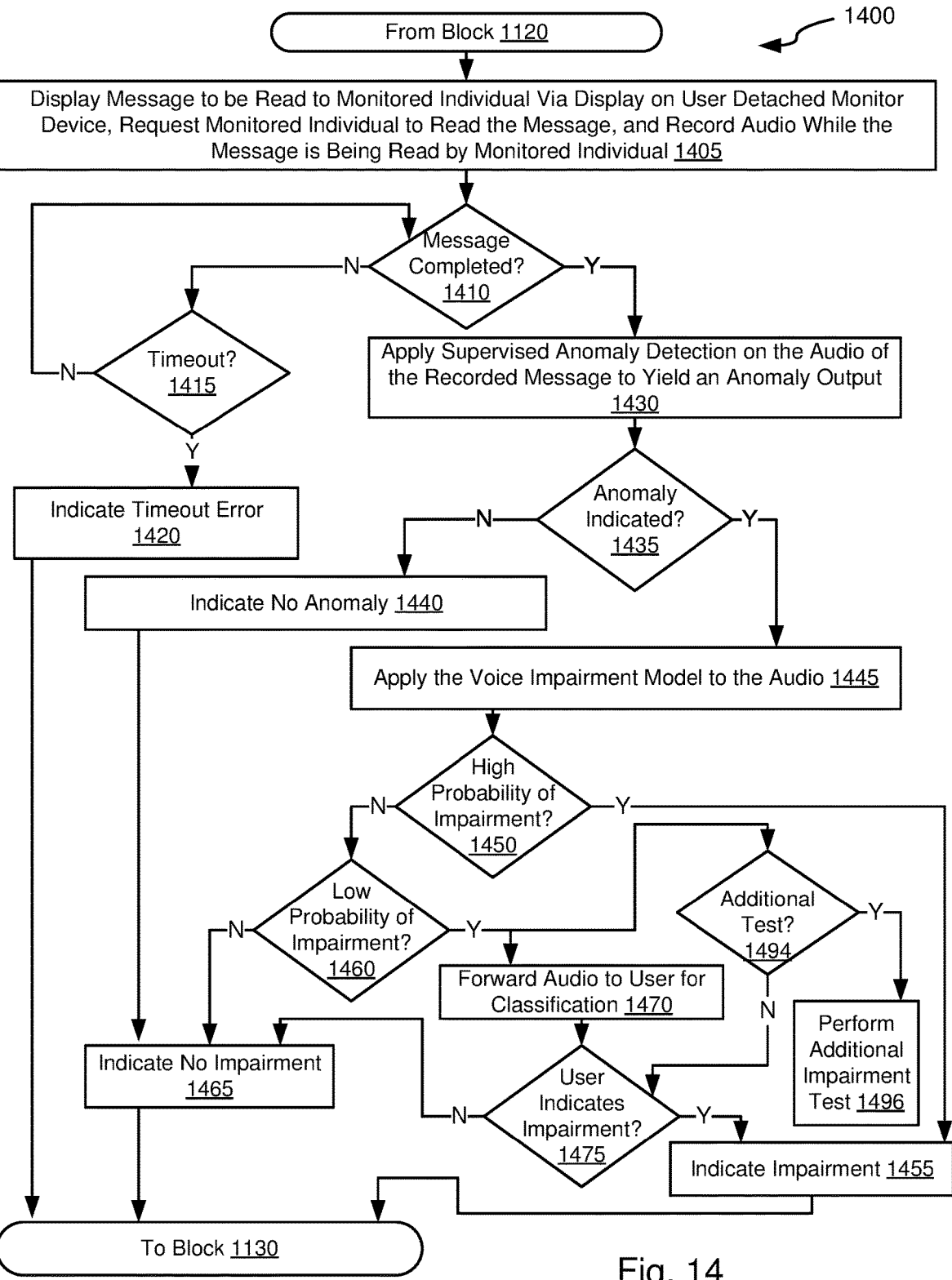
FIG. 14 is a flow diagram showing a method in accordance with various embodiments for determining impairment based upon voice recordings.

Turning to FIG. 14, a flow diagram 1400 shows a method in accordance with various embodiments for determining impairment based upon voice recordings. Flow diagram 1400 represents block 1125 and thus begins from block 1120 of the previously described FIG. 11. The processes of flow diagram 1400 may be executed on user detached monitor device 120 and/or a combination of user detached monitor device 120 and one of central monitoring system 2000 or central monitoring system 2100. Following flow diagram 1400, a message is displayed to the monitored individual using visual display and touch screen 116 of user detached monitor device 120 (block 1405). The message requests the monitored individual to read the message and record audio of them reading the message. The audio can be recorded using microphone 171 of user detached monitor device 120.

It is determined whether the monitored individual has completed reading and recording the message (block 1410). Where the message has not been completed (block 1410), it is determined whether a timeout condition has been met (block 1415). A monitored individual is given a defined time period to comply with the request, and after the defined time period has passed the timeout condition is met. If the timeout condition has been met (block 1415), a timeout error is indicated (block 1420) and the processing returns to block 1130 of FIG. 11 without rendering an analysis of whether the monitored individual is impaired by alcohol.

Alternatively, where it is determined that the message has been completed (block 1410), an anomaly detection is performed on the recorded message (block 1430). Such anomaly detection may be performed by any machine learning process designed to detect anomalous sounds in the user's voice. As such, the anomaly detection is performed by a machine learning model that has been trained with a number of instances of the monitored individual's voice that were recorded when the monitored individual was not impaired. In some embodiments, such voice data is collected as discussed above in relation to FIG. 10. Based upon the disclosure provided herein, one of ordinary skill in the art will recognize a variety of types of machine learning models that may be trained to perform voice anomaly detection in relation to different embodiments.

Where an anomaly is not detected in the monitored individual's voice data (i.e., the monitored individual sounds the same as they always sound) (block 1435), no anomaly is indicated (block 1440) and no impairment is indicated (block 1465). At this juncture, the processing returns to block 1130 of FIG. 11 without rendering an analysis of whether the monitored individual is impaired.

Alternatively, where an anomaly is detected (i.e., the monitored individual sounds different from the way they always sound) (block 1435), a voice impairment model is applied to the recorded message to yield an indication of whether the monitored individual is impaired by, for example, drugs or alcohol (block 1445). The voice impairment model may be implemented in, for example, voice based classification engine 2130 or voice based classification engine 197 depending upon the particular implementation. As discussed above in relation to FIG. 9, the voice impairment model is trained using a number of previously classified voice based impairment data. The voice based impairment data may be derived from a large number of different monitored individuals, and have been classified as either indicating impairment or not. In some cases the classification is based upon a user input 2002 of central monitoring system 2000 or user input 2102 of central monitoring system 2100. In other cases, the classification is based upon the output from the voice impairment model. In some embodiments, the voice impairment model is a TensorFlow™ backbone used to generate a model that can be exported to a selected platform. Based upon the disclosure provided herein, one of ordinary skill in the art will recognize a variety of machine learning model types that may be trained using recorded audio data from tested individuals to determine whether a newly recorded message shows whether an individual is impaired or not.

The output from the voice impairment model indicates a likelihood that the monitored individual is impaired based upon patterns in the audio received from the monitored individual. It is determined whether the likelihood value received from the voice impairment model is higher than a high probability value (block 1450). Such a high probability value is selected as high enough to warrant indicating impairment without having a human user consider the recently received recorded message from the monitored individual. In some embodiments the high probability value is user programmable. Where the likelihood value received from the voice impairment model is higher than the high probability value (block 1450), impairment of the monitored individual is indicated and reported (block 1455) and the processing returns to block 1130 of FIG. 11.

Where, on the other hand, the likelihood value received from the voice impairment model is not higher than the high probability value (block 1450), it is determined whether the likelihood value received from the voice impairment model is lower than a low probability value (block 1460). Such a low probability value is selected as low enough to warrant indicating no impairment without having a human user consider the recently received recorded message. In some embodiments the low probability value is user programmable. Where the likelihood value received from the voice impairment model is lower than the low probability value (block 1460), no impairment is indicated or reported (block 1465) and the processing returns to block 1130 of FIG. 11.

Alternatively, where the likelihood value received from the voice impairment model is not lower than the low probability value (block 1460), an ambiguous condition has occurred. In such a situation, the recently received recorded message is forwarded to a user capable of classifying the data as indicative of impairment or not (block 1470). The user may be, for example, a human responsible for making final determinations of impairment based at least in part upon the recorded voice message. In some cases, the human may be a supervising authority of the monitored individual. This process may forward the recorded voice message to a central monitoring system (e.g., central monitoring system 2100) which is capable of presenting the data to a user and storing the recorded voice message and user classification together in a database. Where the user indicates impairment (block 1475) the impairment is indicated and reported (block 1455), and the processing returns to block 1130 of FIG. 11. Alternatively, where the user indicates no impairment (block 1475), no impairment is indicated or reported (block 1465) and the processing returns to block 1130 of FIG. 11.

In some embodiments, where the likelihood value received from the drug impairment model is not lower than the low probability value (block 1460) indicating the aforementioned ambiguous condition has occurred, it is determined if an additional impairment test should be run (block 1494). Where an additional impairment test is to be run (block 1494), one or more additional impairment tests are performed (block 1496). The additional impairment test(s) may include one or more of: an alcohol impairment test similar to that discussed herein in relation to FIG. 12, a movement based impairment test similar to that discussed herein in relation to FIG. 15, a facial image based impairment test similar to that discussed herein in relation to FIG. 16, and/or a drug based impairment test similar to that discussed herein in relation to FIG. 17.

Figure 15:
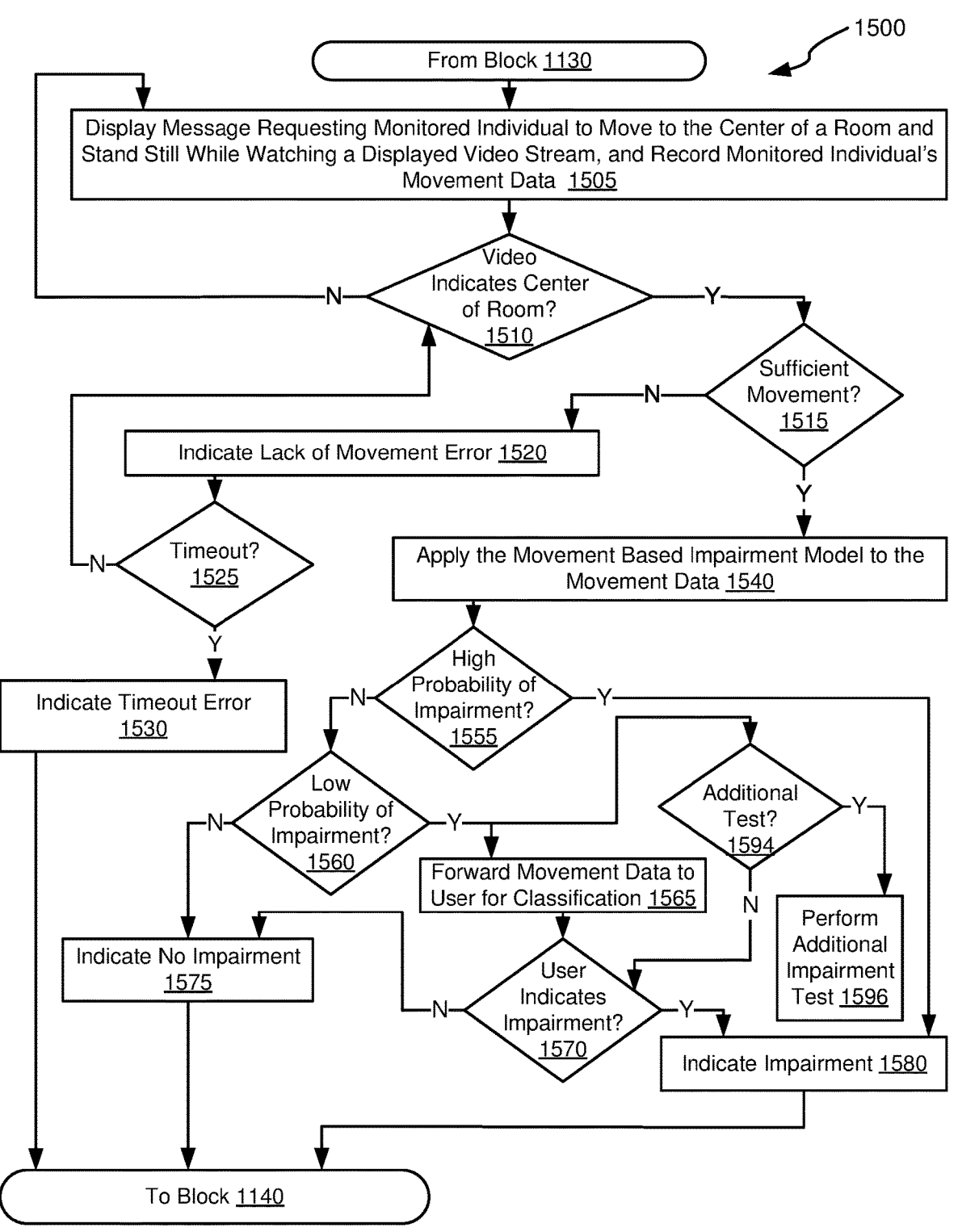
FIG. 15 is a flow diagram showing a method in accordance with various embodiments for determining impairment based upon movement information.

Turning to FIG. 15 a flow diagram 1500 shows a method in accordance with various embodiments for determining impairment based upon movement information. Flow diagram 1400 represents block 1135 and thus begins from block 1130 of the previously described FIG. 11. The processes of flow diagram 1500 may be executed on user detached monitor device 120 and/or a combination of user detached monitor device 120 and one of central monitoring system 2000 or central monitoring system 2100. Following flow diagram 1500, a message is displayed to the monitored individual using visual display and touch screen 116 of user detached monitor device 120 (block 1505). The message requests the monitored individual move to the center of a room where there are no supports, and stand still while watching a disorienting video stream on visual display and touch screen 116. The disorienting video stream may be, but is not limited to, two concentric rings rotating in opposite directions. Based upon the disclosure provided herein, one of ordinary skill in the art will recognize a variety of disorienting video streams that may be used in relation to different embodiments. While the user is watching the disorienting video stream, the movement data of the monitored individual is recorded as recorded movement data. The movement data may be sensed by motion detector 111 of user detached monitor device 120 and recorded to memory 124 by controller circuit 122.

It is determined whether video received from forward camera 172 of user detached monitor device 120 shows that the monitored individual is located at the center of a room away from supports and that the monitored individual is looking at visual display and touch screen 116 of user detached monitor device 120 (block 1510). Once the video indicates that the monitored individual is complying (block 1510), it is determined whether sufficient the recorded movement data indicates sufficient movement (block 1515). When standing still there is almost always some movement unless the monitored individual is improperly relying upon some type of support. Thus, the system looks for a defined threshold of movement. This defined threshold may be user programmable, and in some embodiments the defined threshold is specific to the monitored individual.

Where insufficient movement is detected (block 1515), such is indicated as an error (block 1520) and a timeout condition is tested (block 1525). A monitored individual is given a defined time period to comply with the request, and after the defined time period has passed the timeout condition is met. If the timeout condition has been met (block 1525), a timeout error is indicated (block 1530) and the processing returns to block 1140 of FIG. 11 without rendering an analysis of whether the monitored individual is impaired.

Alternatively, where sufficient movement is detected (block 1515), a movement impairment model is applied to the recorded movement data to yield an indication of whether the monitored individual is impaired by, for example, drugs or alcohol (block 1540). The movement impairment model may be implemented in, for example, movement based classification engine 2135 or movement based classification engine 198 depending upon the particular implementation. As discussed above in relation to FIG. 7, the movement impairment model is trained using a number of previously classified recorded movement data sets. The movement based impairment data may be derived from a large number of different monitored individuals, and have been classified as either indicating impairment or not. In some cases the classification is based upon a user input 2002 of central monitoring system 2000 or user input 2102 of central monitoring system 2100. In other cases, the classification is based upon the output from the movement impairment model. In some embodiments, the movement impairment model is a TensorFlow™ backbone used to generate a model that can be exported to a selected platform. Based upon the disclosure provided herein, one of ordinary skill in the art will recognize a variety of machine learning model types that may be trained using recorded audio data from tested individuals to determine whether a newly recorded message shows whether an individual is impaired or not.

The output from the movement impairment model indicates a likelihood that the monitored individual is impaired based upon movement of the monitored individual when they are expected to be standing still. It is determined whether the likelihood value received from the movement impairment model is higher than a high probability value (block 1555). Such a high probability value is selected as high enough to warrant indicating impairment without having a human user consider the recently received recorded movement data from the monitored individual. In some embodiments the high probability value is user programmable. Where the likelihood value received from the movement impairment model is higher than the high probability value (block 1555), impairment of the monitored individual is indicated and reported (block 1580) and the processing returns to block 1140 of FIG. 11.

Where, on the other hand, the likelihood value received from the movement impairment model is not higher than the high probability value (block 1555), it is determined whether the likelihood value received from the movement impairment model is lower than a low probability value (block 1560). Such a low probability value is selected as low enough to warrant indicating no impairment without having a human user consider the recently received movement data. In some embodiments the low probability value is user programmable. Where the likelihood value received from the movement impairment model is lower than the low probability value (block 1560), no impairment is indicated or reported (block 1575) and the processing returns to block 1140 of FIG. 11.

Alternatively, where the likelihood value received from the movement impairment model is not lower than the low probability value (block 1560), an ambiguous condition has occurred. In such a situation, the recently received recorded movement data is forwarded to a user capable of classifying the data as indicative of impairment or not (block 1565). The user may be, for example, a human responsible for making final determinations of impairment based at least in part upon the movement data. In some cases, the human may be a supervising authority of the monitored individual. This process may forward the recorded movement data to a central monitoring system (e.g., central monitoring system 2100) which is capable of presenting the data to a user and storing the movement data and user classification together in a database. Where the user indicates impairment (block 1570) the impairment is indicated and reported (block 1580), and the processing returns to block 1140 of FIG. 11.

Alternatively, where the user indicates no impairment (block 1570), no drug impairment is indicated or reported (block 1575) and the processing returns to block 1140 of FIG. 11.

In some embodiments, where the likelihood value received from the drug impairment model is not lower than the low probability value (block 1560) indicating the aforementioned ambiguous condition has occurred, it is determined if an additional impairment test should be run (block 1594). Where an additional impairment test is to be run (block 1594), one or more additional impairment tests are performed (block 1596). The additional impairment test(s) may include one or more of: an alcohol impairment test similar to that discussed herein in relation to FIG. 12, a voice based impairment test similar to that discussed herein in relation to FIG. 14, a facial image based impairment test similar to that discussed herein in relation to FIG. 16, and/or a drug based impairment test similar to that discussed herein in relation to FIG. 17.

Figure 16:
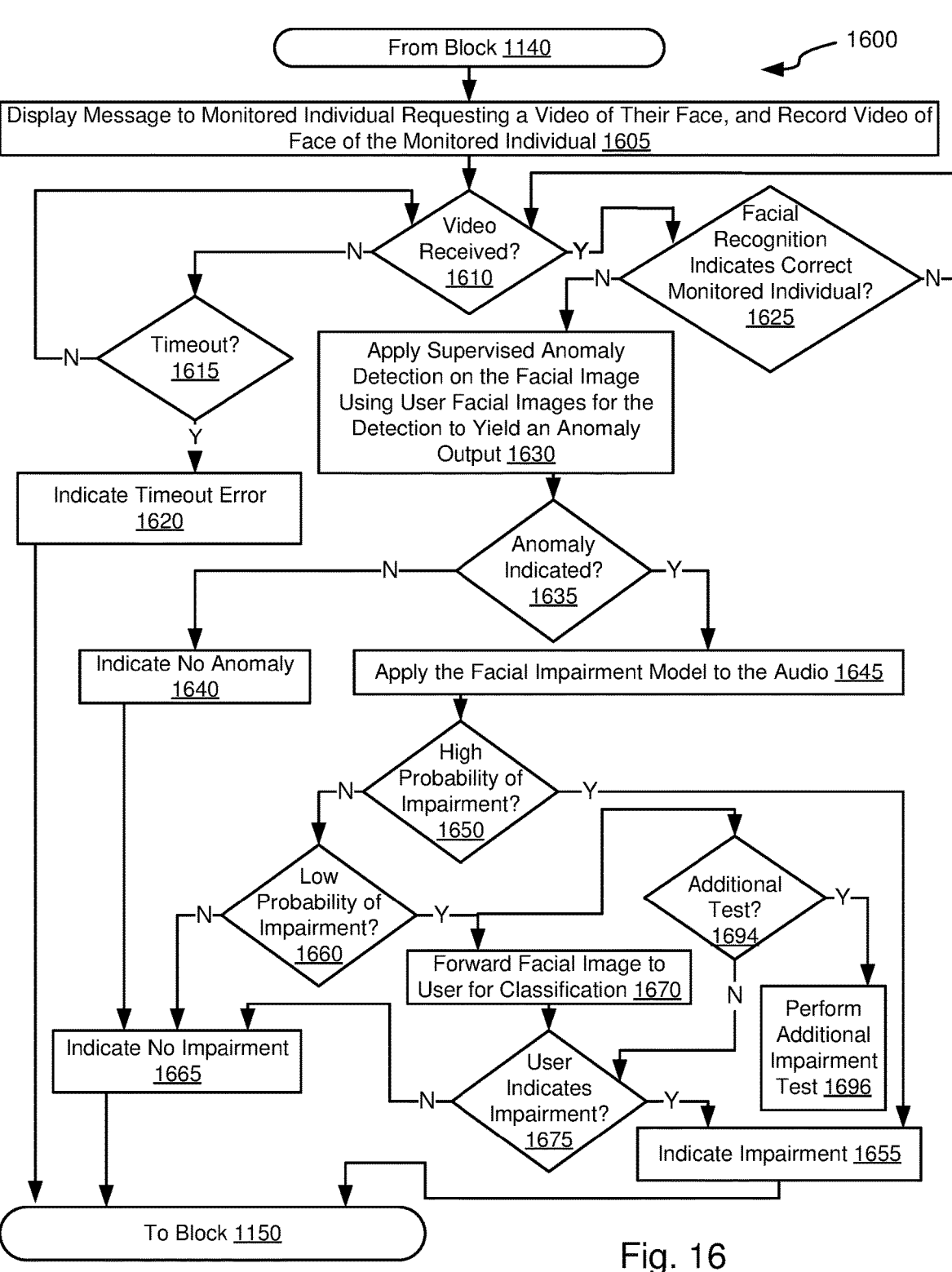
FIG. 16 is a flow diagram showing a method in accordance with various embodiments for determining impairment based upon facial images.

Turning to FIG. 16, a flow diagram 1600 shows a method in accordance with various embodiments for determining impairment based upon facial images. Flow diagram 1600 represents block 1145 and thus begins from block 1140 of the previously described FIG. 11. The processes of flow diagram 1600 may be executed on user detached monitor device 120 and/or a combination of user detached monitor device 120 and one of central monitoring system 2000 or central monitoring system 2100. Following flow diagram 1600, a message is displayed to the monitored individual using visual display and touch screen 116 of user detached monitor device 120 (block 1605). The message requests the monitored individual to record a video of their face using forward camera 172. A still image of the monitored individual's face is recorded as a recorded face image.

It is determined whether the monitored individual has completed recording a video of their face (block 1610). Where a recorded face image is not yet available (block 1610), it is determined whether a timeout condition has been met (block 1615). A monitored individual is given a defined time period to comply with the request, and after the defined time period has passed the timeout condition is met. If the timeout condition has been met (block 1615), a timeout error is indicated (block 1620) and the processing returns to block 1150 of FIG. 11 without rendering an analysis of whether the monitored individual is impaired by alcohol.

Alternatively, where it is determined that the recorded face image is available (block 1610), an anomaly detection is performed on the recorded face image (block 1630). Such anomaly detection may be performed by any machine learning process designed to detect anomalous elements of an individual's face. As such, the anomaly detection is performed by a machine learning model that has been trained with a number of instances of the monitored individual's face image that were recorded when the monitored individual was not impaired. In some embodiments, such voice data is collected as discussed above in relation to FIG. 6. Based upon the disclosure provided herein, one of ordinary skill in the art will recognize a variety of types of machine learning models that may be trained to perform voice anomaly detection in relation to different embodiments.

Where an anomaly is not detected in the monitored individual's face image (i.e., the monitored individual appears the same as they always appear) (block 1635), no anomaly is indicated (block 1640) and no impairment is indicated or reported (block 1665). At this juncture, the processing returns to block 1150 of FIG. 11 without rendering an analysis of whether the monitored individual is impaired.

Alternatively, where an anomaly is detected (i.e., the monitored individual appears different from the way they always appear) (block 1635), a facial impairment model is applied to the recorded message to yield an indication of whether the monitored individual is impaired by, for example, drugs or alcohol (block 1645). The facial impairment model may be implemented in, for example, facial image based classification engine 2140 or visual based classification engine 199 depending upon the particular implementation. As discussed above in relation to FIG. 5, the facial impairment model is trained using a number of previously classified face images. The facial impairment data may be derived from a large number of different monitored individuals, and have been classified as either indicating impairment or not. In some cases the classification is based upon a user input 2002 of central monitoring system 2000 or user input 2102 of central monitoring system 2100. In other cases, the classification is based upon the output from the facial impairment model. In some embodiments, the facial impairment model is a TensorFlow™ backbone used to generate a model that can be exported to a selected platform. Based upon the disclosure provided herein, one of ordinary skill in the art will recognize a variety of machine learning model types that may be trained using facial image data from tested individuals to determine whether a newly recorded message shows whether an individual is impaired or not.

The output from the facial impairment model indicates a likelihood that the monitored individual is impaired based upon features in the still face image received from the monitored individual. It is determined whether the likelihood value received from the facial impairment model is higher than a high probability value (block 1650). Such a high probability value is selected as high enough to warrant indicating impairment without having a human user consider the recently received face image from the monitored individual. In some embodiments the high probability value is user programmable. Where the likelihood value received from the facial impairment model is higher than the high probability value (block 1650), impairment of the monitored individual is indicated and reported (block 1655) and the processing returns to block 1150 of FIG. 11.

Where, on the other hand, the likelihood value received from the facial impairment model is not higher than the high probability value (block 1650), it is determined whether the likelihood value received from the facial impairment model is lower than a low probability value (block 1660). Such a low probability value is selected as low enough to warrant indicating no impairment without having a human user consider the recently received face image. In some embodiments the low probability value is user programmable. Where the likelihood value received from the facial impairment model is lower than the low probability value (block 1660), no impairment is indicated or reported (block 1665) and the processing returns to block 1150 of FIG. 11.

Alternatively, where the likelihood value received from the facial impairment model is not lower than the low probability value (block 1660), an ambiguous condition has occurred. In such a situation, the recently received face image is forwarded to a user capable of classifying the data as indicative of impairment or not (block 1670). The user may be, for example, a human responsible for making final determinations of impairment based at least in part upon the recently received face image. In some cases, the human may be a supervising authority of the monitored individual. This process may forward the face image to a central monitoring system (e.g., central monitoring system 2100) which is capable of presenting the data to a user and storing the face image and user classification together in a database. Where the user indicates impairment (block 1675) the impairment is indicated and reported (block 1655), and the processing returns to block 1150 of FIG. 11. Alternatively, where the user indicates no impairment (block 1675), no impairment is indicated or reported (block 1665) and the processing returns to block 1150 of FIG. 11.

In some embodiments, where the likelihood value received from the drug impairment model is not lower than the low probability value (block 1660) indicating the aforementioned ambiguous condition has occurred, it is determined if an additional impairment test should be run (block 1694). Where an additional impairment test is to be run (block 1694), one or more additional impairment tests are performed (block 1696). The additional impairment test(s) may include one or more of: an alcohol impairment test similar to that discussed herein in relation to FIG. 12, a voice based impairment test similar to that discussed herein in relation to FIG. 14, a movement based impairment test similar to that discussed herein in relation to FIG. 15, and/or a drug based impairment test similar to that discussed herein in relation to FIG. 17.

Figure 17A:
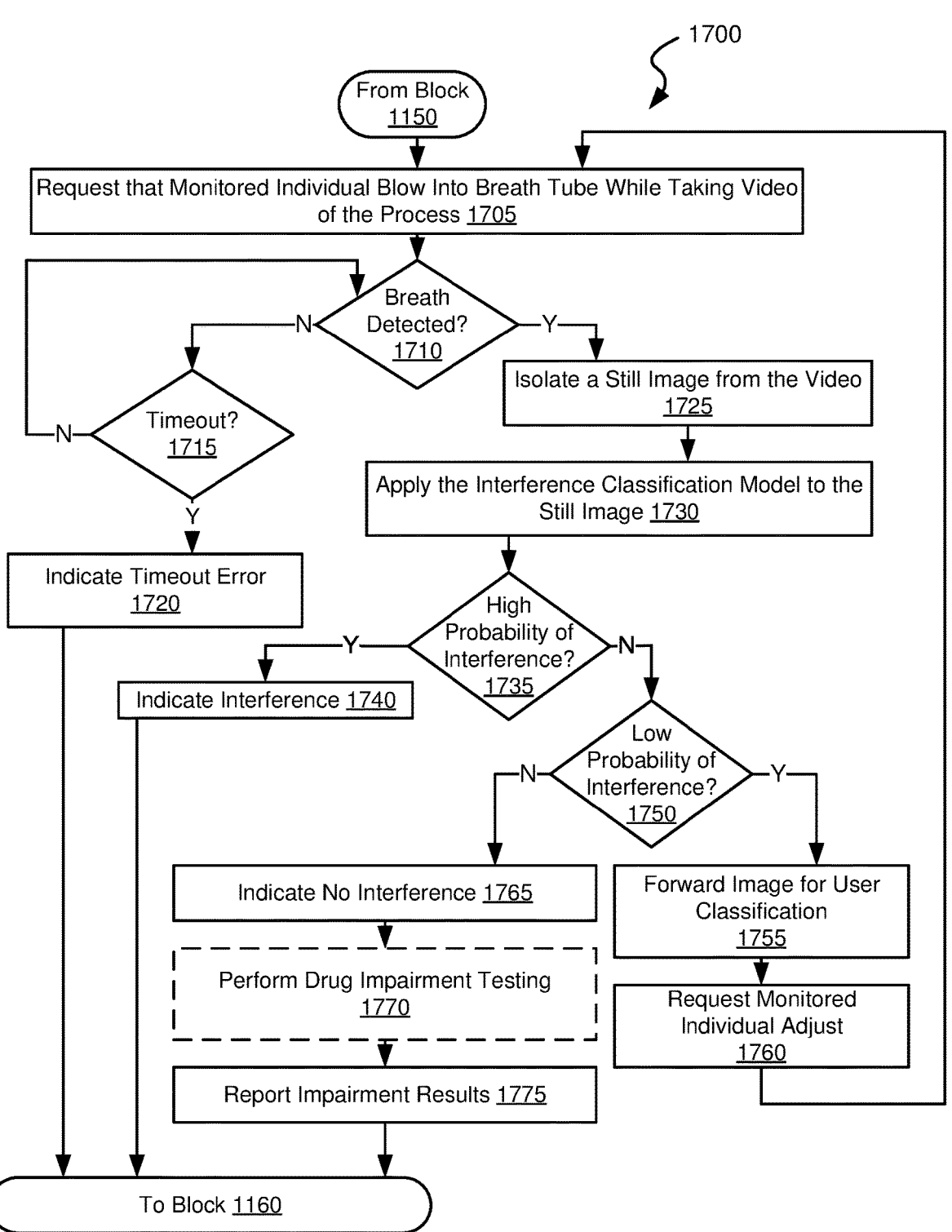
FIGS. 17*a*-17*b* are flow diagrams showing a method in accordance with some embodiments for detecting drug based impairment.
Figure 17B:
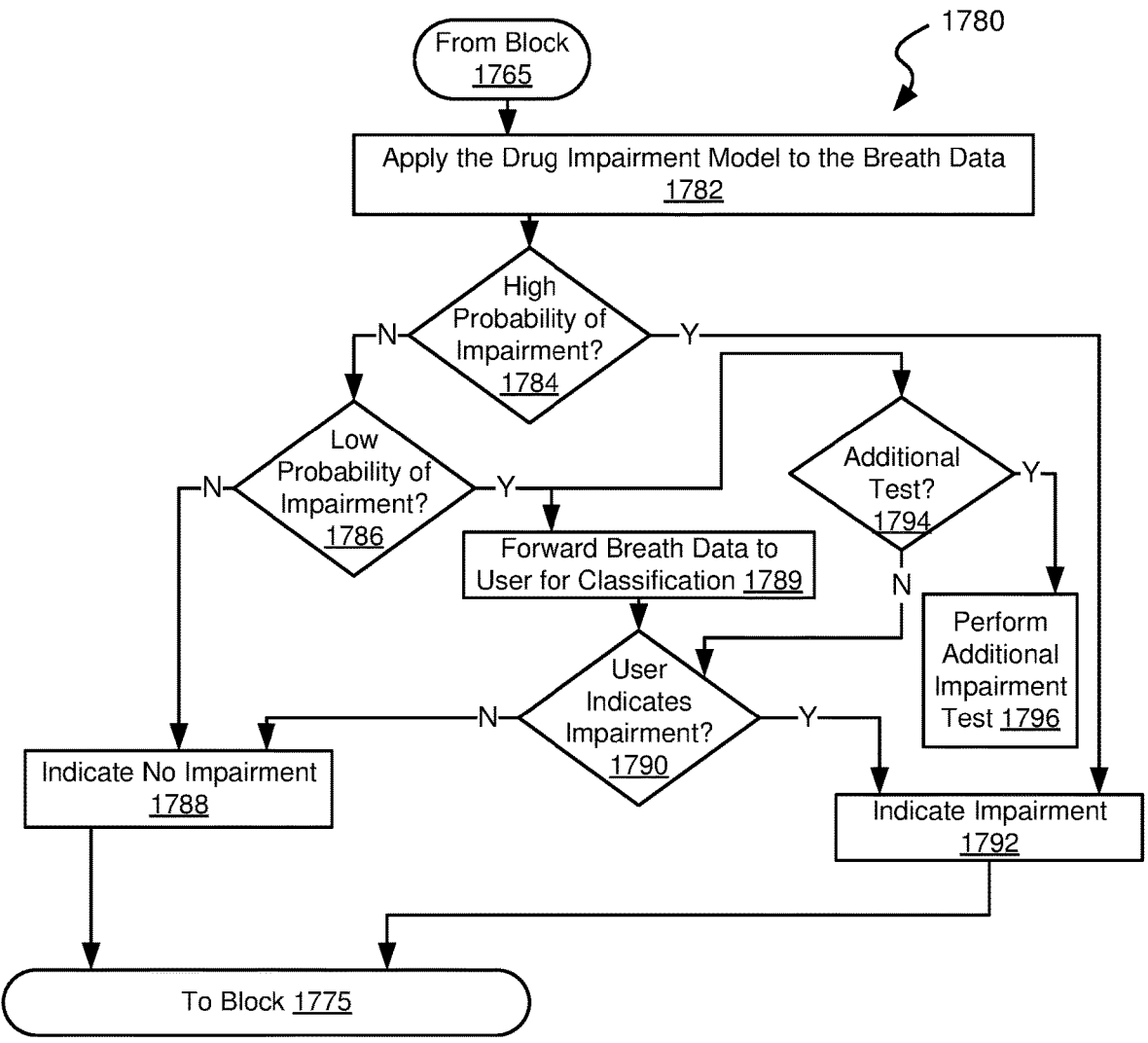

Turning to FIGS. 17a-17b, flow diagram 1700 and flow diagram 1780 together show a method in accordance with various embodiments for determining impairment based upon breath VOC measurements. Flow diagram 1700 and flow diagram 1780 together represent block 1155 and thus begins from block 1150 of the previously described FIG. 11. The processes of flow diagram 1700 and flow diagram 1780 may be executed on one of user detached monitor device 120 or breath based impairment detection device 192 depending upon the system implementation, and/or a combination of one of user detached monitor device 120 or breath based impairment detection device 192 and one of central monitoring system 2000 or central monitoring system 2100. Turning to FIG. 17a and following flow diagram 1700, a request is made for the monitored individual to blow into breath tube 190 while taking a video using one of forward camera 172 or reverse camera 173 of user detached monitor device including the monitored individual's face and surrounding region while blowing (block 1705). This request may be provided via a display on either or both of user detached monitor device 120 and/or breath based impairment detection device 192.

A sensor on breath based impairment detection device 192 detects whether at least a minimum gas flow is reported from breath tube 190 (block 1710). This sensing may be done using any sensor known in the art for detecting gas flow volume. The sensor may be included as part of breath sensor 166 in breath based impairment detection device 192, with the information from the sensor being provided to one or both of alcohol impairment classification engine 168 and/or drug impairment classification engine 169. Where it is determined that insufficient gas flow has been detected by the sensor (block 1710), it is determined whether a timeout condition has been met (block 1715). A monitored individual is given a defined time period to comply with the request, and after the defined time period has passed the timeout condition is met. If the timeout condition has been met (block 1720), a timeout error is indicated (block 1720) and the processing returns to block 1160 of FIG. 11 without rendering an analysis of whether the monitored individual is impaired by drugs.

Alternatively, where it is determined that sufficient gas flow has been detected by the sensor (block 1710), a still image from the video of the monitored individual's face and surrounding area is isolated (block 1725). An interference classification model is applied to the still image to yield an indication of whether the monitored individual is interfering with breath tube (block 1730). As discussed above in relation to FIG. 3, the interference classification model is trained using a number of previously classified images showing a monitored individual while they are breathing into breath tube 190. The images may be derived from a large number of different monitored individuals, and have been classified as either indicating interference with breath tube 190 or no interference with breath tube 190. In some cases the classification is based upon a user input 2002 of central monitoring system 2000 or user input 2102 of central monitoring system 2100. In other cases, the classification is based upon the output from the user classification model. FIG. 13a are drawings representing a number of example still images 1302, 1304, 1306, 1308, 1310 each showing an respective individual with a breath tube properly inserted in their mouth while breathing, and without any addition elements included in the image that appear to be interfering with the test. FIG. 13b are drawings representing a number of example still images 1352, 1354, 1356, 1358 each showing an respective individual interfering with a breath tube. Still image 1352 shows an individual with both the breath tube and a secondary tube inserted into their mouth. In such an approach, a gas can be blown into the individual's mouth that flows out through the breath tube simulating breath. Still image 1354 shows an individual with the breath tube inserted in their mouth, and a secondary tube connected to into the breath tube. In such an approach, a gas can be blown from the secondary tube into the breath tube simulating breath. Still image 1356 shows an individual with the breath tube inserted in their mouth, but their hand is over their mouth and their head is turned potentially hiding a secondary tube. Still image 1356 shows an individual with the breath tube near their mouth along with a secondary tube. In such an approach, a gas can be blown toward the individual's mouth from the secondary tube and into the breath tube simulating breath.

In some embodiments, the interference classification model is a TensorFlow™ backbone used to generate a model that can be exported to a selected platform. Based upon the disclosure provided herein, one of ordinary skill in the art will recognize a variety of machine learning model types that may be trained using images of individuals blowing in a breath tube to determine whether a newly received image shows an individual properly using the breath tube.

The output from the interference classification model indicates a likelihood that the monitored individual is interfering with breath tube 190 or not using it properly. It is determined whether the likelihood value received from the interference classification model is higher than a high probability value (block 1735). Such a high probability value is selected as high enough to warrant indicating interference without having a human user consider the image. In some embodiments the high probability value is user programmable. Where the likelihood value received from the interference classification model is higher than the high probability value (block 1735), an interference is indicated (block 1740) and the processing returns to block 1160 of FIG. 11 without rendering an analysis of whether the monitored individual is impaired by drugs.

Where, on the other hand, the likelihood value received from the interference classification model is not higher than the high probability value (block 1735), it is determined whether the likelihood value received from the interference classification model is lower than a low probability value (block 1750). Such a low probability value is selected as low enough to warrant indicating no interference without having a human user consider the image. In some embodiments the low probability value is user programmable. Where the likelihood value received from the interference classification model is lower than the low probability value (block 1750), no interference is indicated (block 1765). In this situation, drug impairment testing applied to the received breath sample (block 1770). Block 1770 is shown in dashed lines as it is depicted in more detail in flow diagram 1780 of FIG. 17*b*.

Turning to FIG. 17*b* and following flow diagram 1780, a drug impairment model is applied to the breath data received from the sensor to yield an indication of whether the monitored individual is impaired by drugs (block 1782). The received breath data includes a type quantity of VOCs found in the monitored individual's breath sample. The drug impairment model may be implemented in, for example, breath drug based classification engine 2150 or drug impairment classification engine 169 depending upon the particular implementation. As discussed above in relation to FIG. 4, the drug impairment model is trained using a number of previously classified breath data sets corresponding to monitored individuals. The breath data sets may be derived from a large number of different monitored individuals, and have been classified as either indicating drug impairment or not. In some cases the classification is based upon a user input 2002 of central monitoring system 2000 or user input 2102 of central monitoring system 2100. In other cases, the classification is based upon the output from the drug impairment model. In some embodiments, the drug impairment model is a TensorFlow™ backbone used to generate a model that can be exported to a selected platform. Based upon the disclosure provided herein, one of ordinary skill in the art will recognize a variety of machine learning model types that may be trained using breath data sets sampled from the breath of individuals blowing in a breath tube to determine whether a newly received breath data set shows whether an individual is drug impaired or not.

The output from the drug impairment model indicates a likelihood that the monitored individual is drug impaired based upon VOCs in the breath data derived from the monitored individual. It is determined whether the likelihood value received from the drug impairment model is higher than a high probability value (block 1784). Such a high probability value is selected as high enough to warrant indicating drug impairment without having a human user consider the recently received breath data set from the monitored individual. In some embodiments the high probability value is user programmable. Where the likelihood value received from the drug impairment model is higher than the high probability value (block 1784), drug impairment of the monitored individual is indicated (block 1792) and the processing returns to block 1775 of FIG. 17*a* where the indication is used and/or reported.

Where, on the other hand, the likelihood value received from the drug impairment model is not higher than the high probability value (block 1784), it is determined whether the likelihood value received from the drug impairment model is lower than a low probability value (block 1786). Such a low probability value is selected as low enough to warrant indicating no drug impairment without having a human user consider the breath data set. In some embodiments the low probability value is user programmable. Where the likelihood value received from the drug impairment model is lower than the low probability value (block 1786), no drug impairment is indicated (block 1788) and the processing returns to block 1775 of FIG. 17*a* where the indication is used and/or reported.

Alternatively, where the likelihood value received from the drug impairment model is not lower than the low probability value (block 1786), an ambiguous condition has occurred. In such a situation, the recently received breath data is forwarded to a user capable of classifying the data as indicative of drug impairment or not (block 1789). The user may be, for example, a human responsible for making final determinations of drug impairment based at least in part upon the VOC data. In some cases, the human may be a supervising authority of the monitored individual. This process may forward the breath to a central monitoring system (e.g., central monitoring system 2100) which is capable of presenting the data to a user and storing the breath data and user classification together in a database. Where the user indicates impairment (block 1790) the impairment is indicated (block 1792) and the processing returns to block 1775 of FIG. 17*a* where the indication is used and/or reported. Alternatively, where the user indicates no impairment (block 1790), no drug impairment is indicated (block 1788) and the processing returns to block 1775 of FIG. 17*a* where the indication is used and/or reported.

In some embodiments, where the likelihood value received from the drug impairment model is not lower than the low probability value (block 1786) indicating the aforementioned ambiguous condition has occurred, it is determined if an additional impairment test should be run (block 1794). Where an additional impairment test is to be run (block 1794), one or more additional impairment tests are performed (block 1796). The additional impairment test(s) may include one or more of: a voice based impairment test similar to that discussed herein in relation to FIG. 14, a movement based impairment test similar to that discussed herein in relation to FIG. 14, a facial image based impairment test similar to that discussed herein in relation to FIG. 16, or a breath alcohol based impairment test similar to that discussed herein in relation to FIG. 12. Returning to FIG. 17*a*, the received impairment results (block 1792 or block 1788) are reported (block 1775). Having reported the impairment results, the process then returns to block 1160 of FIG. 11.

Figure 18:
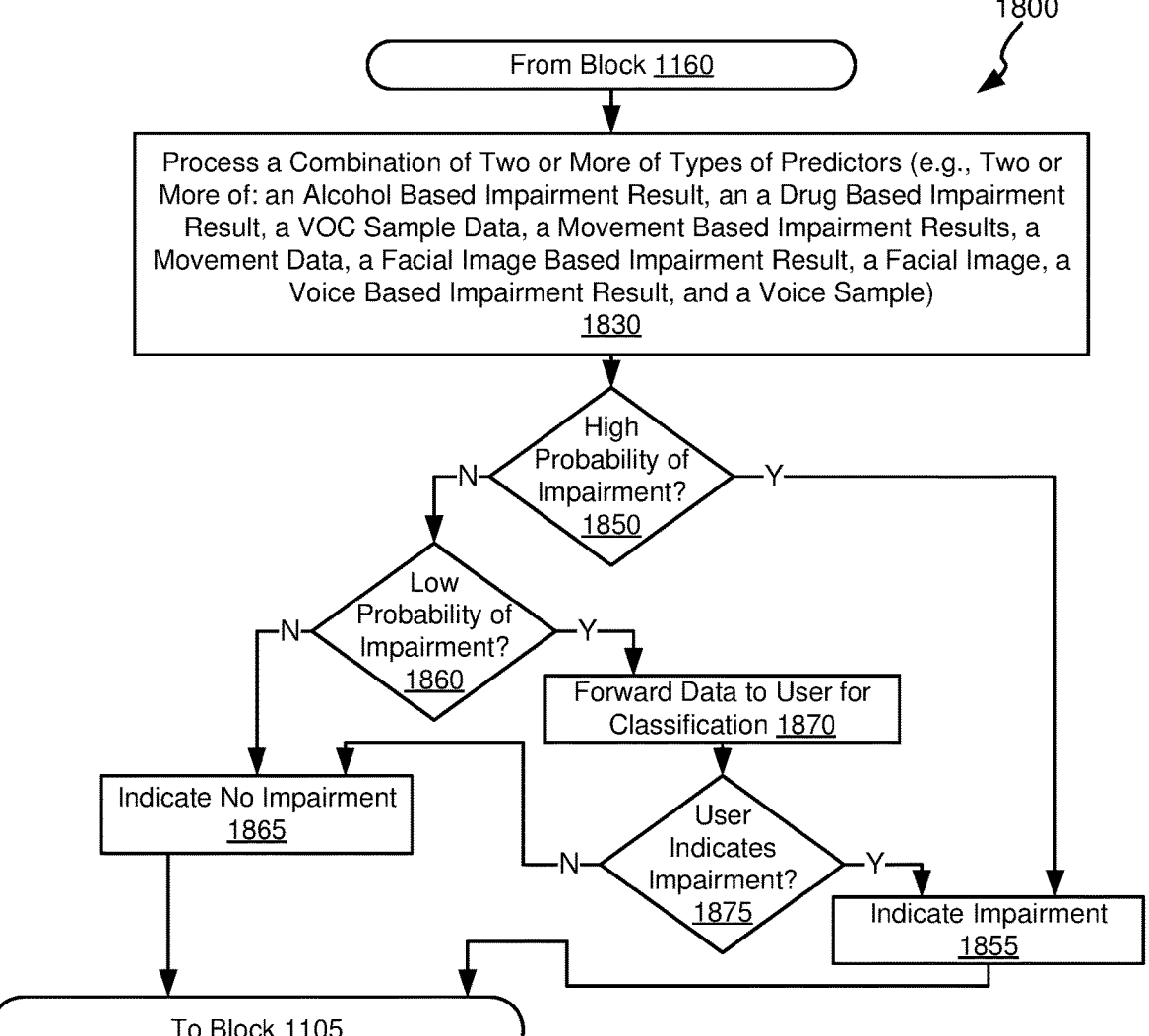
FIG. 18 is a flow diagram showing a method in accordance with some embodiments for applying a multi-predictor machine learning model that is configured to yield an impairment classification based upon two or more different types of data provided as respective predictors to the multi-predictor machine learning model.

Turning to FIG. 18, a flow diagram 1800 shows a method in accordance with some embodiments for applying a multi-predictor machine learning model that is configured to yield an impairment classification based upon two or more different types of data provided as respective predictors to the multi-predictor machine learning model. Flow diagram 1800 represents block 1165 and thus begins from block 1160 of the previously described FIG. 11. The processes of flow diagram 1800 may be executed on user detached monitor device 120 and/or a combination of user detached monitor device 120 and one of central monitoring system 2000 or central monitoring system 2100. The processes rely upon a multi-predictor machine learning model that may be implemented, for example, as part of multi-predictor classification engine 2160, or multi-predictor classification engine 2050.

Following flow diagram 1800, a combination of two or more types of predictors are provided to a multi-predictor machine learning model (block 1830). Any of the two or more types of predictors may by themselves be useful in classifying whether an individual is impaired, but the two or more are used together in the multi-predictor machine learning model to enhance the accuracy of the classification of impairment or non-impairment. As just some examples, the two or more types of predictors may include two or more of: an alcohol based impairment result (e.g., an impairment result reported as part of block 1275 of FIG. 12), a drug based impairment result (e.g., an impairment result reported as part of block 1788 or block 1792 of FIG. 17*b*), breath data (e.g., the breath data used in relation to block 1782 of FIG. 17*b*), a voice based impairment result (e.g., an impairment result reported as part of either block 1455 or block 1465 of FIG. 14), voice data (e.g., the recorded message discussed in relation to block 1405 of FIG. 14), a movement based impairment result (e.g., an impairment result reported as part of either block 1580 or block 1575 of FIG. 15), movement data (e.g., the recorded movement data discussed in relation to block 1505 of FIG. 15), a facial image based impairment result (e.g., an impairment result reported as part of either block 1655 or block 1665 of FIG. 16), a facial image (e.g., the facial image discussed in relation to block 1605 of FIG. 16). The processing includes applying a machine learning model to the combination of the two or more predictors to yield a likelihood that an individual is impaired.

It is determined whether the likelihood value received from the multi-predictor machine learning model is higher than a high probability value (block 1850). Such a high probability value is selected as high enough to warrant indicating impairment without having a human user consider any of the predictors. In some embodiments the high probability value is user programmable. Where the likelihood value received from the multi-predictor machine learning model is higher than the high probability value (block 1850), impairment of the monitored individual is indicated and reported (block 1855) and the processing returns to block 1105 of FIG. 11.

Where, on the other hand, the likelihood value received from the multi-predictor machine learning model is not higher than the high probability value (block 1950), it is determined whether the likelihood value received from the multi-predictor machine learning model is lower than a low probability value (block 1860). Such a low probability value is selected as low enough to warrant indicating no impairment without having a human user consider the recently received predictors. In some embodiments the low probability value is user programmable. Where the likelihood value received from the multi-predictor machine learning model is lower than the low probability value (block 1860), no impairment is indicated or reported (block 1865) and the processing returns to block 1105 of FIG. 11.

Alternatively, where the likelihood value received from the multi-predictor machine learning model is not lower than the low probability value (block 1860), an ambiguous condition has occurred. In such a situation, the recently received predictors are forwarded to a user capable of classifying the data as indicative of impairment or not (block 1870). The user may be, for example, a human responsible for making final determinations of impairment based at least in part upon the recently received face image. In some cases, the human may be a supervising authority of the monitored individual. This process may forward the face image to a central monitoring system (e.g., central monitoring system 2100) which is capable of presenting the data to a user and storing the predictors and user classification together in a database. Where the user indicates impairment (block 1875) the impairment is indicated and reported (block 1855), and the processing returns to block 1105 of FIG. 11. Alternatively, where the user indicates no impairment (block 1875), no impairment is indicated or reported (block 1865) and the processing returns to block 1105 of FIG. 11.

In conclusion, the present invention provides for novel systems, devices, and methods for monitoring individuals.

While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A system for detecting drug based impairment, the system comprising:
   a breath input device;
   a breath sensor configured to receive a breath sample of an individual via the breath input device and to provide a sample value corresponding to the breath sample;
   one or more processors;
   a non-transient computer readable medium coupled to the one or more processors, and having stored therein instructions which when executed by the one or more processors, causes the one or more processors to:
   receive the sample value;
   apply a drug impairment model to the sample value to yield a probability that the individual is impaired;
   indicate an impairment when the probability exceeds a first threshold; and
   indicate no impairment when the probability is less than a second threshold.

2. The system of claim 1, wherein the probability is a first probability, the system further comprising:
   a camera; and
   wherein the non-transient computer readable medium further having stored therein instructions which when executed by the one or more processors, causes the one or more processors to:
   receive an image captured by the camera of the individual blowing into the breath input device;
   apply an interference classification model to the image to yield a second probability that the individual is interfering with gas flowing from a mouth of the individual via the breath input device;
   indicate an interference when the second probability exceeds a third threshold; and
   cause a request to be sent to the individual to modify use of the breath input device when the second probability exceeds a third threshold.

3. The system of claim 1, the system further comprising:
   a camera; and
   wherein the non-transient computer readable medium further having stored therein instructions which when executed by the one or more processors, causes the one or more processors to:
   receive a facial image of the individual captured by the camera; and
   perform a facial image based impairment test using the facial image.

4. The system of claim 1, wherein the sample value is a first sample value, wherein the breath sensor is further configured to provide a second sample value corresponding to the breath sample, and wherein the non-transient computer readable medium further having stored therein instructions which when executed by the one or more processors, causes the one or more processors to perform a breath alcohol based impairment test using the second sample value.

5. The system of claim 1, wherein the sample value is a level of a volatile organic compound.

6. The system of claim 5, wherein the volatile organic compound is selected from a group consisting of a volatile organic compound indicative of methamphetamine, a volatile organic compound indicative of marijuana, a volatile organic compound indicative of cocaine, and a volatile organic compound indicative of heroin.

7. The system of claim 1, wherein the non-transient computer readable medium further having stored therein instructions which when executed by the one or more processors, causes the one or more processors to forward the sample value for classification when the probability is both less than the first threshold and greater than the second threshold.

8. The system of claim 1, wherein the non-transient computer readable medium further having stored therein instructions which when executed by the one or more processors, causes the one or more processors to cause a request to be sent to the individual to perform an additional impairment test.

9. The system of claim 8, wherein the additional impairment test is selected from a group consisting of: a voice based impairment test, and a movement based impairment test.

10. The system of claim 1, wherein the sample value is a first sample value, wherein the breath sensor is further configured to provide a second sample value corresponding to the breath sample, and wherein the non-transient computer readable medium further having stored therein instructions which when executed by the one or more processors, causes the one or more processors to perform a breath alcohol based impairment test using the second sample value.

11. The system of claim 1, wherein the non-transient computer readable medium further having stored therein instructions which when executed by the one or more processors, causes the one or more processors to perform an additional impairment test when the probability is both less than the first threshold and greater than the second threshold, wherein the additional impairment test is selected from a group consisting of: a voice based impairment test, a movement based impairment test, a facial image based impairment test, and a breath alcohol based impairment test.

12. The system of claim 1, wherein the non-transient computer readable medium further having stored therein instructions which when executed by the one or more processors, causes the one or more processors to report the impairment to a recipient device apart from the one or more processors.

13. The system of claim 1, wherein the drug impairment model is a machine learning model trained using breath samples that have each been classified as exhibiting a volatile organic compound corresponding a controlled substance.

14. A method for detecting use of a controlled substance, the method comprising:

processing, by a breath sensor, a breath sample received from an individual;

providing, by the breath sensor, a sample value corresponding to the breath sample;

applying, by a processor, a drug impairment model to the sample value to yield a probability that the individual is impaired;

indicating, by the processor, a usage when the probability exceeds a first threshold; and indicating, by the processor, no usage when the probability is less than a second threshold.

15. The method of claim 14, wherein the probability is a first probability, the method further comprising:

receiving, by the processor, an image captured by a camera of the individual blowing into a breath input device;

applying, by the processor, an interference classification model to the image to yield a second probability that the individual is interfering with gas flowing from a mouth of the individual via the breath input device;

indicating, by the processor, an interference when the second probability exceeds a third threshold; and causing, by the processor, a request to be sent to the individual to modify use of the breath input device when the second probability exceeds a third threshold.

16. The method of claim 14, wherein the sample value is a level of a volatile organic compound.

17. The method of claim 16, wherein the volatile organic compound is selected from a group consisting of: a volatile organic compound indicative of methamphetamine, a volatile organic compound indicative of marijuana, a volatile organic compound indicative of cocaine, and a volatile organic compound indicative of heroin.

18. The method of claim 14, the method further comprising: causing, by the processor, a request to be sent to the individual to perform an additional impairment test.

19. The method of claim 18, wherein the additional impairment test is selected from a group consisting of: a voice based impairment test, and a movement based impairment test.

20. A non-transient computer readable medium having stored therein instructions, which when executed by a hardware processing system cause the hardware processing system to:

receive a sample value, wherein the sample value is generated by a breath sensor based upon a breath sample received from an individual via a breath input device;

apply a drug impairment model to the sample value to yield a probability that the individual is impaired;

indicate an impairment when the probability exceeds a first threshold; and indicate no impairment when the probability is less than a second threshold.

* * * * *